US011666780B2

(12) United States Patent
Marsteller

(10) Patent No.: US 11,666,780 B2
(45) Date of Patent: Jun. 6, 2023

(54) METHODS, SYSTEMS, AND COMPOSITIONS FOR MAINTAINING FUNCTIONING DRAINAGE BLEBS ASSOCIATED WITH MINIMALLY INVASIVE MICRO SCLEROSTOMY

(71) Applicant: RADIANCE THERAPEUTICS, INC., Tucson, AZ (US)

(72) Inventor: Laurence J. Marsteller, Tucson, AZ (US)

(73) Assignee: RADIANCE THERAPEUTICS, INC., Tucson, AZ (US)

( * ) Notice: Subject to any disclaimer, the term of this patent is extended or adjusted under 35 U.S.C. 154(b) by 896 days.

(21) Appl. No.: 16/584,737

(22) Filed: Sep. 26, 2019

(65) Prior Publication Data

US 2020/0101318 A1 Apr. 2, 2020
US 2021/0379403 A9 Dec. 9, 2021

Related U.S. Application Data

(63) Continuation-in-part of application No. PCT/US2018/049400, filed on Sep. 4, 2018.
(Continued)

(30) Foreign Application Priority Data

Sep. 7, 2017 (GB) .................................... 1714392

(51) Int. Cl.
  *A61N 5/10* (2006.01)
  *A61M 1/00* (2006.01)
(52) U.S. Cl.
  CPC ............. *A61N 5/1017* (2013.01); *A61M 1/84* (2021.05); *A61M 2210/0612* (2013.01)

(58) Field of Classification Search
  CPC .................. A61N 5/1017; A61M 1/84; A61M 2210/0612
  See application file for complete search history.

(56) References Cited

U.S. PATENT DOCUMENTS 1,525,158 A   2/1925  Viol
1,733,159 A  10/1929  Leach
(Continued)

FOREIGN PATENT DOCUMENTS

CA         643082 A    6/1962
DE        1149134 B    5/1963
(Continued)

OTHER PUBLICATIONS

Howlet J et al., Journal of Current Glaucoma Practice 2014, 8(2):63-66.
(Continued)

*Primary Examiner* — Susan S Su
*Assistant Examiner* — Eric Rassavong
(74) *Attorney, Agent, or Firm* — Nguyen Tarbet LLC

(57) ABSTRACT

Methods, systems, and compositions for maintaining functioning drainage blebs to reduce intraocular pressure (IOP) of an eye being treated for glaucoma. The methods, systems, and compositions feature the combination of a minimally invasive micro sclerostomy (MIMS) procedure and the application of beta radiation to a target area. The beta radiation can function to inhibit or reduce the inflammation and/or fibrogenesis that typically occurs after a MIMS procedure and leads to hole and/or bleb failure. By reducing inflammation and/or fibrogenesis, the MIMS holes and/or blebs can remain functioning appropriately.

26 Claims, 15 Drawing Sheets

Related U.S. Application Data

(60) Provisional application No. 62/738,573, filed on Sep. 28, 2018.

(56) References Cited

U.S. PATENT DOCUMENTS

| | | | |
|---|---|---|---|
| 2,517,568 A * | 8/1950 | Hissong | A61F 9/007 600/7 |
| 2,559,793 A * | 7/1951 | Pregel | G21G 4/06 600/7 |
| 5,637,073 A * | 6/1997 | Freire | A61N 5/1017 600/3 |
| D387,162 S | 12/1997 | Zeimer | |
| 6,050,970 A | 4/2000 | Baerveldt | |
| D441,447 S | 5/2001 | Hjertman et al. | |
| 6,274,614 B1 | 8/2001 | Richter et al. | |
| 6,443,881 B1 | 9/2002 | Finger | |
| 6,875,165 B2 | 4/2005 | Dejuan, Jr. et al. | |
| 7,070,554 B2 | 7/2006 | White et al. | |
| D621,508 S | 8/2010 | Bindra | |
| D642,266 S | 6/2011 | Marsteller et al. | |
| 8,430,804 B2 | 4/2013 | Brigatti et al. | |
| D691,270 S | 10/2013 | Marsteller et al. | |
| 8,602,959 B1 * | 12/2013 | Park | A61N 5/1017 600/7 |
| D702,346 S | 4/2014 | Ben Nun | |
| D731,058 S | 6/2015 | Dietrich | |
| D731,060 S | 6/2015 | Little, III | |
| D747,806 S | 1/2016 | Wargner et al. | |
| D752,749 S | 3/2016 | Van Dalen et al. | |
| D755,970 S | 5/2016 | Bergmanson | |
| D756,515 S | 5/2016 | Chin et al. | |
| D795,427 S | 8/2017 | Korenfeld et al. | |
| 10,022,558 B1 * | 7/2018 | Marsteller | A61N 5/1017 |
| D933,225 S | 10/2021 | Marsteller et al. | |
| D933,226 S | 10/2021 | Marsteller et al. | |
| 2002/0115902 A1 | 8/2002 | DeJuan, Jr. | |
| 2004/0138515 A1 | 7/2004 | White | |
| 2005/0277802 A1 | 12/2005 | Larsen et al. | |
| 2006/0111605 A1 * | 5/2006 | Larsen | A61N 5/1017 600/1 |
| 2007/0265485 A1 | 11/2007 | DeJuan, Jr. et al. | |
| 2008/0300444 A1 | 12/2008 | Ye et al. | |
| 2009/0124955 A1 * | 5/2009 | Ayyala | A61F 9/0017 604/521 |
| 2009/0216062 A1 | 8/2009 | Axelrod et al. | |
| 2010/0000449 A1 | 1/2010 | Brigatti et al. | |
| 2010/0004581 A1 * | 1/2010 | Brigatti | A61N 5/1017 604/20 |
| 2011/0004045 A1 | 1/2011 | Larsen et al. | |
| 2013/0006033 A1 | 1/2013 | Cipriani et al. | |
| 2013/3000603 | 1/2013 | Cirpriani et al. | |
| 2013/0211178 A1 | 8/2013 | Brigatti et al. | |
| 2015/0105605 A1 | 4/2015 | Finger et al. | |
| 2015/0265850 A1 | 9/2015 | Finger et al. | |
| 2016/0151643 A1 | 6/2016 | Roder | |
| 2017/0112520 A1 | 4/2017 | Lavi et al. | |
| 2017/0216499 A1 * | 8/2017 | Kaplan | A61B 90/39 |
| 2017/0258988 A1 * | 9/2017 | Meyer | A61M 5/168 |
| 2018/0229055 A1 * | 8/2018 | Marsteller | A61N 5/1017 |
| 2018/0296855 A1 | 10/2018 | Lohrenz et al. | |
| 2019/0240504 A1 | 8/2019 | Brachman et al. | |
| 2019/0290643 A1 | 9/2019 | Ni et al. | |
| 2020/0101318 A1 | 4/2020 | Marsteller | |
| 2020/0171323 A1 | 6/2020 | Marsteller et al. | |
| 2020/0197725 A1 | 6/2020 | Marsteller | |

FOREIGN PATENT DOCUMENTS

| | | | | |
|---|---|---|---|---|
| EP | 1529554 A1 * | 5/2005 | | A61N 5/1017 |
| EP | 1529554 B1 | 2/2006 | | |
| EP | 1997532 A1 | 12/2008 | | |
| EP | 3031494 A1 * | 6/2016 | | A61B 17/00234 |
| EP | 3031494 B1 | 8/2018 | | |
| FR | 4398 E | 7/1905 | | |
| GB | 2551706 A | 1/2018 | | |
| JP | S63138962 A | 6/1988 | | |
| JP | 2001507969 A | 6/2001 | | |
| JP | 2011508654 A | 3/2011 | | |
| JP | 2016512101 A | 4/2016 | | |
| RU | 134056 U1 | 11/2013 | | |
| WO | WO9850092 | 11/1998 | | |
| WO | WO200158346 A1 | 8/2001 | | |
| WO | 2004098523 A2 | 11/2004 | | |
| WO | WO-2004098523 A2 * | 11/2004 | | A61N 5/1017 |
| WO | 2005079915 A1 | 9/2005 | | |
| WO | WO-2005079915 A1 * | 9/2005 | | A61N 5/1017 |
| WO | 2009075714 A1 | 6/2009 | | |
| WO | WO-2009075714 A1 * | 6/2009 | | A61N 5/1017 |
| WO | 2009149175 A1 | 12/2009 | | |
| WO | WO-2009149175 A1 * | 12/2009 | | A61N 5/1007 |
| WO | 2010022153 A1 | 2/2010 | | |
| WO | WO-2010022153 A1 * | 2/2010 | | A61N 5/1017 |
| WO | WO2013186779 A2 | 12/2013 | | |
| WO | WO2015057531 A2 | 4/2015 | | |
| WO | WO2015105539 A3 | 7/2015 | | |
| WO | WO2016178746 A1 | 11/2016 | | |
| WO | WO2017112891 A1 | 6/2017 | | |
| WO | WO2018060983 A1 | 4/2018 | | |
| WO | WO2019050863 A1 | 3/2019 | | |
| WO | WO2019164940 A1 | 8/2019 | | |

OTHER PUBLICATIONS

NRC Information Notice 96-66: United States Nuclear Regulatory Commission, Office of Nuclear Material Safety and Safeguards, Washington D.C. 20555, Dec. 13, 1996.

K. Nilsen, PhD, Department of Physics and Scientific Computing Group University of Oslo, N-0316 Oslo, Norway in Spring 2008.

Schultz et al. Growth Factors and Ocular Wound Healing. Eye (1994) 8, 184-187.

Kirwan et al. Beta irradiation: new uses for an old treatment: a review. Eye(2003) 17, 207-215.

Khaw et al. Modulation of wound healing after glaucoma surgery. Curr Opin Ophthalmol. Apr. 2001;12(2):143-8.

Sanoculis MIMS Procedure. http://www.sanoculis.com/category/mims-procedure.

Kumar et al. Minimally invasive micro sclerostomy may be alternative to trabeculectomy. Ocular Surgery News U.S. Edition, May 10, 2016 . https://www.healio.com/ophthalmology/glaucoma/news/print/ocular-surgery-news/%7Be1be2619-cca2-40cb-8ff4-28062463f4ee%7D/minimally-invasive-micro-sclerostomy-may-be-alternative-to-trabeculectomy.

Cook et al. Randomised clinical trial of trabeculectomy with mitomycin-C versus trabeculectomy with beta radiation. SA Ophthalmology Journal, Spring 2018 • vol. 13 | No. 4. pp. 11-14.

Peter Egbert, Glaucoma in west Africa: a neglected problem, Br J Ophthalmol 2002, 86, pp. 131-132.

P T Khaw, S Ward, I Grievson, N S C Rice, Effect of Beta radiation on proliferation human Tenon's capsule fibroblasts, Br J Ophthalmology, 1991, 75, 580-583.

R Wilder, et. al. Pterygium treated with excision and postoperative beta irradiation, Int. J. Radiation Oncology Viol. Phys., 1992, vol. 23, pp. 533-537.

James F Kirwan, Christina Rennie, Jennifer R Evans, Beta radiation for glaucoma surgery (Review), Cochrane Database of Systematic reviews 2012, Issue 6. Art. No.: CD003433, published Jun. 13, 2012. http://www.cochrane.org/CD003433/EYES_beta-radiation-in-glaucoma-surgery.

G Hay-Smith, J Kiran, C Usher, I E Murdoch, Beta radiation: an effective and potentially cheap aid to preventing sight loss from glaucoma, 2010 . Conference proceedings. https://www.semanticscholar.org/paper/Beta-radiation%3A-an-effective-and-potentially-cheap-Hay-Smith-Kirwan/7da123cef3f6203697a584af35561ae3d00306a1 https://pdfs.semanticscholar.org/7da1/23cef3f6203697a584af35561ae3d00306a1.pdf.

Jimmy S. Lai, Agnes S. Poon, Clement C.Tham, Dennis S. Lam, Ophthalmology, Sep. 2003, vol. 110, Issue 9, pp. 1822-1826. https://www.ncbi.nlm.nih.gov/pubmed/13129883.

(56) References Cited

OTHER PUBLICATIONS

H A Quigley, AT Broman, The number of people with glaucoma worldwide in 2010 and 2020, Br J Ophthalmol 2006 (90) 262-267.

C D Mpyet, S K Alli, N E Zaure, Site of trabeculectomy and control of intraocular pressure: a preliminary report, The Nigerian Joural of Surgical research vol. 4, No. 3-5, Jul.-Dec. 2002, pp. 94-97.

J F Kirwan, S Cousins, L Venter, C Cook, a Stunting, P Roux, I Murdoch, BMJ, Effect of beta radiation on success of glaucoma drainage surgery in South Africa: randomized controlled trial, doi:10.1136/bmj.38971.395301.7C (published Oct. 5, 2006).

R George, R S Ve, L Vijaya, Glaucoma in India: estimated burden of disease, J. Glaucoma, vol. 19, No. 6, pp. 391-397.

R J Venkatesh, K Palanisway, Glaucoma care in India, Glaucoma Today, Jan./Feb. 2013, pp. 37-39.

Kazim Dhalla, Simon Cousens, Richard Bowman, Mark Wood, Ian Murdoch, PLOS One, Sep. 8, 2016. http://journals.plos.org/plosone/article?id=10.1371/journal.pone.0161674.

R George, L Vijaya, Prevalence of glaucoma in India: a review, J of Current Glaucoma Practice, Spetdec 2007I 1(2) pp. 7-11.

Technical Information and Instruction Manual for users of Beta Therapy Source Model 67-850, Nuclear Associates, Carle Place, N.Y. Copyright 1979.

Strontium-90 surface and ophthalmic applicators, from Amersham product manual. Publication year unknown.

Soares CG. Comparison of NIST and manufacturer calibrations of 90Sr+90Y ophthalmic applicators. Med Phys 1995, 22(9): 1487-1493.

Bahrassa and Datta. Postoperative beta radiation treatment of pterygium. Int J Radiat Oncol Biol Phys 1983, 9(5):679-84.

Castroviejo. Trans Am Acad Ophthalmol Otolaryngol. 1956, 60(3):486.

Zhang et al., In Vivo Cross-Sectional Observation and Thickness Measurement of Bulbar Conjunctiva Using Optical Coherence Tomography. Investigative Ophthalmology & Visual Science 2011, 52(10):7787-7791.

Wells AP, Ashraff NN, Hall RC, et al. Comparison of two clinical bleb grading systems. Ophthalmology 2006;113:77-83. Abstract.

Dhingra S, Khaw PT. The Moorfields Safer Surgery System. Middle East African Journal of Ophthalmology. 2009;16(3):112-115.

Invitation to Pay Additional Fees issued for PCT Application No. PCT/US18/49400 on Nov. 1, 2018.

UKIPO Examination Opinion and Search Report issued for GB Application No. GB1714392.6 dated Feb. 16, 2018.

Constable et al. "The effects of single doses of beta radiation on the wound healing behaviour of human Tenon's capsule fibroblasts" Br J OphthalmoL 2004; 88:169-173 (doi:1 0.1136lbjo.2003.020388).

Assmann et al. "Biodegradable radioactive implants for glaucoma filtering surgery produced by ion implantation" Nucl Instrum Meth B. 2007; 257(1-2):108-113 (doi:10.1016/j.nimb.2006.12.155).

International Search Report issued for PCT Application No. PCT/US18/49400 dated Jan. 2, 2019.

Ayyala et al. Early Follow-Up After Xen Implantation Needed. Ocular Surgery News U.S. Edition, Mar. 5, 2018. https://www.healio.com/ophthalmology/glaucoma/news/online/%7B4f090e9a-4661-42a7-a8b7-4fa0cd690316%7D/early-follow-up-after-xen-implantation-needed.

Ayyala et al. Xen Gel Stent Early Results: Safety and Efficacy in the Short Term. AGS 2018 Annual Meeting. Mar. 1-4. https://ags.planion.com/Web.User/AbstractDet?ACCOUNT=AGS&CONF=AM18&ABSID=11997.

Erickson et al. "The American College of Radiology and the American Brachytherapy Society practice parameter for the performance of radionuclide-based high-dose-rate brachytherapy." Brachytherapy 16.1 (2017): 75-84.

Schultz et al. "Growth factors and ocular wound healing." Eye 8.2 (1994): 184-187.

Kirwan et al. "Beta irradiation: new uses for an old treatment: a review." Eye 17.2 (2003): 207-215.

Khaw et al. "Modulation of wound healing after glaucoma surgery." Current opinion in ophthalmology 12.2 (2001): 143-148.

Sanoculis LTD, MIMS Procedure. http://www.sanoculis.com/category/mims-procedure (2014) 2 pages.

Kumar et al. Minimally invasive micro sclerostomy may be alternative to trabeculectomy. Ocular Surgery News U.S. Edition, May 10, 2016, 4 pages.

Cook et al. "Randomised clinical trial of trabeculectomy with mitomycin-C versus trabeculectomy with beta radiation." South African Ophthalmology Journal 13.4 (2018): 11-14.

Egbert, "Glaucoma in West Africa: a neglected problem." British journal of ophthalmology 86.2 (2002): 131-132.

Khaw et al. "Effect of beta radiation on proliferating human Tenon's capsule fibroblasts." British journal of ophthalmology 75.10 (1991): 580-583.

Wilder, el. al. "Pterygium treated with excision and postoperative beta irradiation." International Journal of Radiation Oncology* Biology* Physics 23.3 (1992): 533-537.

Kirwan et al. "Beta radiation in glaucoma surgery (Review)" Cochrane Database of Systematic Reviews (2012).

G Hay-Smith et al. "Beta radiation: an effective and potentially cheap aid to preventing sight loss from glaucoma, 2010." Conference proceedings. 3 pages.

Lai et al. "Trabeculectomy with β radiation: Long-term follow-up." Ophthalmology 110.9 (2003): 1822-1826.

Quigley et al. "The number of people with glaucoma worldwide in 2010 and 2020." British journal of ophthalmology 90.3 (2006): 262-267.

Mpyet et al. "Site of trabeculectomy and control of intraocular pressure: a preliminary report." Nigerian Journal of Surgical Research 4.3 (2002): 94-97.

Kirwan et al. "Effect of ß radiation on success of glaucoma drainage surgery in South Africa: randomised controlled trial." Bmj 333.7575 (2006): 942.

George et al. "Glaucoma in India: estimated burden of disease." Journal of glaucoma 19.6 (2010): 391-397.

Venkatesh et al. "Glaucoma care in India." Glaucoma Today (2013): 37-39.

Dhalla et al. "Is beta radiation better than 5 flurouracil as an adjunct for trabeculectomy surgery when combined with cataract surgery? A randomised controlled trial." PloS one 11.9 (2016): e0161674.

George et al. "Prevalence of glaucoma in India: a review." J Curr Glaucoma Pract 1.2 (2007): 7-11.

Technical Information and Instruction Manual for users of Beta Therapy Source Model 67-850, Nuclear Associates, Carle Place, NY. Copyright 1979, 14 pages.

Strontium-90 surface and ophthalmic applicators, from Amersham product manual. Publication year unknown. 6 pages.

SOARES "Comparison of NIST and manufacturer calibrations of 90Sr+ 90Y ophthalmic applicators." Medical Physics 22.9 (1995): 1487-1493.

Bahrassa et al "Postoperative beta radiation treatment of pterygium." International Journal of Radiation Oncology* Biology* Physics 9.5 (1983): 679-684.

Castroviejo. "New masks to limit the active surface of radiation in beta ray applicators." Transactions-American Academy of Ophthalmology and Otolaryngology. American Academy of Ophthalmology and Otolaryngology 60.3 (1956): 486.

Zhang et al., "In vivo cross-sectional observation and thickness measurement of bulbar conjunctiva using optical coherence tomography." Investigative ophthalmology & visual science 52.10 (2011): 7787-7791.

Wells et al. "Comparison of two clinical bleb grading systems." Ophthalmology 113.1 (2006): 77-83.

Dhingra et al. "The moorfields safer surgery system." Middle East African journal of ophthalmology 16.3 (2009): 112.

Constable et al. "The effects of single doses of β radiation on the wound healing behaviour of human Tenon's capsule fibroblasts." British journal of ophthalmology 88.2 (2004): 169-173.

Assmann et al. "Biodegradable radioactive implants for glaucoma filtering surgery produced by ion implantation." Nuclear Instruments and Methods in Physics Research Section B: Beam Interactions with Materials and Atoms 257.1-2 (2007): 108-113.

Ayyala et al, Early Follow-Up after Xen Implantation Needed. Ocular Surgery News U.S. Edition, Mar. 5, 2018, 1 page.

(56) References Cited

OTHER PUBLICATIONS

Ayyala et al, Xen Gel Stent Early Results: Safety and Efficacy in the Short Term. AGS 2018 Annual Meeting. Mar. 4, 2 pages.

Howlet et al., "Bulbar conjunctival and Tenon's layer thickness measurement using optical coherence tomography." Journal of current glaucoma practice 8.2 (2014): 63.

NRC "Information Notice 96-66: Recent Misadminitrations Caused by Incorrect Calibrations of Strontium-90 Eye Applicators", United States Nuclear Regulatory Commission, Office of Nuclear Material Safety and Safeguards, Washington D.C. 20555, Dec. 13, 1996, 4 pages.

Nilsen, PhD, Department of Physics and Scientific Computing Group University of Oslo, N-0316 Oslo, Norway in Spring 2008, 14 pages.

Kirwan et al. "Beta radiation in glaucoma surgery" 2012, 2 pages.

J.E. Gentle, Monte Carlo Methods in Statistics, International Encyclopedia of Education (Third Edition) 2010.

Cordeiro, M. F., L. Chang, and P. T. Khaw. "The healing of ocular tissues: The basis of successful treatment of ocular disease." (2000): 101-110.

\* cited by examiner

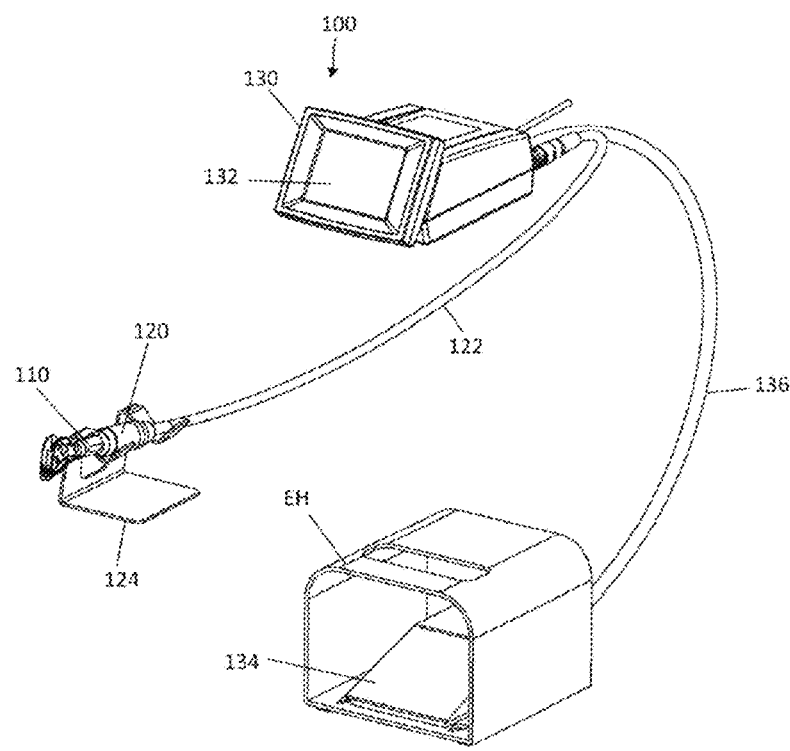
FIG. 2A
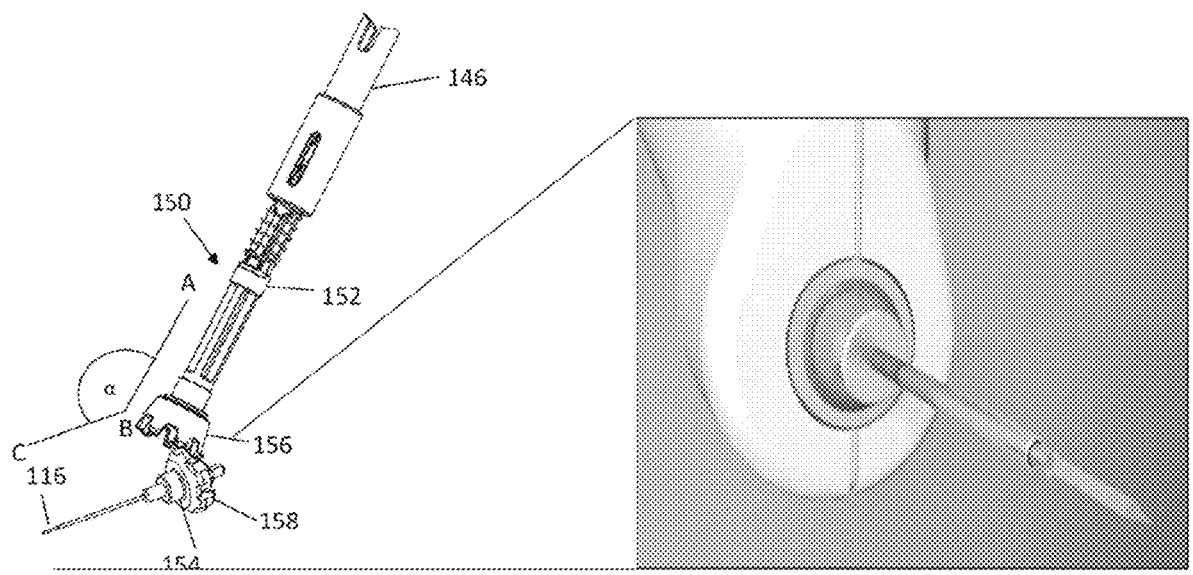
FIG. 2B
FIG. 2C

METHODS, SYSTEMS, AND COMPOSITIONS FOR MAINTAINING FUNCTIONING DRAINAGE BLEBS ASSOCIATED WITH MINIMALLY INVASIVE MICRO SCLEROSTOMY

CROSS-REFERENCES TO RELATED APPLICATIONS

This application is a non-provisional, and claims benefit of U.S. patent application No. 62/738,573 filed Sep. 28, 2018 the specification(s) of which is/are incorporated herein in their entirety by reference. This application is also a continuation-in-part and claims benefit of PCT Application No, PCT/US18/49400 filed Sep. 4, 2018, which claims benefit of UK Patent Application No. 1714392.6 filed Sep. 7, 2017, the specification(s) of which is/are incorporated herein in their entirety by reference.

FIELD OF THE INVENTION

The present invention relates to methods, systems, and compositions for treating glaucoma treatment-associated drainage blebs and/or holes with beta radiation to maintain functioning blebs and/or holes. The present invention also relates to the use of a Minimally Invasive Micro Sclerostomy (MIMS) and beta radiation for treating glaucoma.

BACKGROUND OF THE INVENTION

Glaucoma

Glaucoma is the leading cause of irreversible blindness and represents a family of diseases with a characteristic optic neuropathy. Therapy for this group of diseases is principally focused at reducing the intraocular pressure (IOP) of the fluid inside the eye (aqueous humor), thus averting ongoing damage to the optic nerve.

Glaucoma is managed by attempting to lower the intraocular pressure (IOP). In the USA, Europe, and some other industrialized countries, the first line therapy is typically medication delivered by eye drops. Such medications include beta-blockers, prostaglandins, alpha-adrenergic agonists, and carbonic anhydrase inhibitors. For patients who fail medication and in other parts of the world where there are economic and distribution barriers to the practicality of daily medication and frequent follow up, the treatment regime is primarily surgical interventions.

One way to prevent vision loss from glaucoma is to lower intraocular pressure with drainage surgery that shunts fluid out of the eye through a channel created during a trabeculectomy procedure, by implanting a flow-controlled drainage device during Minimally Invasive Glaucoma Surgery (MIGS), or by the use of other surgical procedures such as Minimally Invasive Micro Sclerostomy (MIMS) or devices. These systems and procedures allow drainage of the aqueous humor from within the eye to a small reservoir (termed a "bleb") under the conjunctiva, from where the aqueous humor is later reabsorbed.

For example, Minimally Invasive Micro Sclerostomy (MIMS) combines the mechanism of conventional trabeculectomy and simple needling. MIMS is a microfluidic full-thickness procedure, guarded by the small diameter of the drainage channel, which was developed as an advancement of laser sclerostomy. This new technique uses a state of the art custom made cutting and drilling device designed so as to reduce trauma to the surrounding tissue.

The MIMS device is a surgical tool comprising a penetration tip to allow the insertion of the tool into the eye tissue; a mechanism for removal of the thin tissue layer; and a shank to enable the coupling of the instrument to the rotating system. A multiuse component is designed to activate the surgical tool in order to remove the corneoscleral tissue by rotary motion. The activation component comprises a controller that manages the activation pulse duration and RPM; a motor; a handpiece that is an interface between the activation component and the surgical tool, which transmits the rotary motion from the motor to the surgical tool; and a footswitch to assist the user to activate the machine. One activation cycle time is 0.1 second, and surgical tool speed is 8,000 RPM.

The MIMS device is inserted under the conjunctiva through the corneoscleral junction and into the anterior chamber. The surgical tool is then rotated to create a 50 µm to 100 µm diameter corneoscleral channel in order to allow for drainage of the aqueous humor from the anterior chamber into the subconjunctival space. To create the corneoscleral channel, a piece of tissue is removed with the surgical tool.

With current glaucoma treatments (e.g., MIMS, MIGS, etc.), scar tissue often compromises the bleb or other surrounding structures (e.g., drainage channels associated with MIMS), ultimately impeding or blocking the flow of excess fluid. Despite compelling therapeutic advantages over non-surgical treatments, drainage surgery and devices are clinically limited by postoperative scarring.

Attempts to address this include the application of anti-metabolites such as mitomycin C (MMC) and 5-fluorouracil (5FU). These antimetabolites are used in liquid form and are delivered either by injection or by placing microsurgical sponges soaked in the drug directly onto the operative site underneath the conjunctiva. One of the problems associated with antimetabolites (e.g., MMC and 5FU) is that they do not preserve blebs well. By some reports, the failure rate by three years approaches 50%.

The present invention provides methods featuring brachytherapy application of beta radiation in combination with procedures such as Minimally Invasive Micro Sclerostomy (MIMS) (and/or the like) to effectively maintain functioning drainage blebs and/or drainage channels, e.g., to help avoid scar formation or wound reversion, to inhibit or reduce the fibrogenesis and/or inflammation in the blebs or holes, etc.

As discussed in detail below, while the use of beta radiation in trabeculectomy-type glaucoma treatment has long been discouraged by experts in the field, it has been found to be surprisingly effective at preventing bleb failure when combined with use of MIMS.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It has been surprisingly discovered that specific methods of treatment and systems that combine Minimally Invasive Micro Sclerostomy (MIMS) or the like and the application of beta radiation are effective for maintaining functioning drainage blebs and/or drainage channels, e.g., by reducing or inhibiting treatment-induced scar formation or wound revision, by inhibiting or reducing fibrogenesis and/or inflammation in the bleb and/or drainage channel, etc. For example, the methods herein describe providing a therapeutic does of beta radiation to the tissues surrounding the MIMS drainage channel and/or the portion of the bleb above the MIMS drainage channel (e.g., the center or around the center of the bleb).

The methods herein are surprisingly effective, given the current treatment for preventing bleb failure is to treat the edges of the bleb with a drug such as mitomycin c. In fact, the emphasis of the previous and current treatments has always been to concentrate treatment towards the edges because the scarring occurs at the edges of the bleb, forming what is known as a ring of iron or scarring ring. Indeed, treatment with mitomycin c involves pushing mitomycin c-soaked sponges towards the edges of the bleb away from the drainage channel (or stent, in the case of MIGS). One of ordinary skill in the art would not be motivated to treat the drainage channel (or stent, in the case of MIGS) to prevent bleb scarring.

Further, there would be no motivation to administer beta radiation to the tissues surrounding the MIMS drainage channel and/or the portion of the bleb above the MIMS drainage channel because the ophthalmology community believes that the fibroblasts that cause scarring are not in the sclera at the MIMS drainage channel. As previously discussed, the scarring occurs around the edges of the bleb, forming the ring of iron or scarring ring. Thus, one of ordinary skill in the art would not be motivated to administer beta radiation to the tissue around the drainage channel (or stent, in the case of MIGS) to prevent bleb scarring.

Unpredictability of the Effects of Beta Radiation on MIMS-Induced Scarring Response There has been no evidence to prove that the scarring responses caused by trabeculectomy surgery and MIMS implantation are the same. In fact, there is a strong suggestion that the responses could be significantly different. Therefore, a person having ordinary skill in the art would not be able to predict how beta radiation would affect the scarring responses caused by a MIMS procedure.

Teaching Away from the Use of Beta Radiation for Glaucoma Treatment

1. Industry expectation that mitomycin C (MMC) is more effective than beta radiation:

It would be surprising to one of ordinary skill in the art that beta radiation would be chosen over liquid antimetabolites because the prior art teaches that beta radiation is a less effective anti-metabolite than mitomycin C (MMC) and is merely similar in effectiveness to 5-fluorouracil (5FU). In brief, beta radiation has been reported to be roughly equivalent to 5FU as an anti-metabolite for glaucoma drainage surgery, and MMC has been reported to be superior to 5FU for the same use. Therefore, MMC is taught to be more effective than beta radiation as an anti-metabolite for glaucoma drainage surgery. More specifically, a 2016 study involving a trabeculectomy-type of glaucoma surgery (Dhalla et al., 2016, PLoS ONE 11(9): e0161674) concluded that: "Firstly, there is no evidence of a difference between the use of 5FU and beta radiation as an anti-metabolite in phacotrabeculectomy surgery." Additionally, a 2015 Cochrane review by Cabourne et al. (Cabourne et al., 2015, Cochrane Database of Systematic Reviews Issue 11. Art. No. CD006259) that compared MMC and 5FU for wound healing in trabeculectomy-type glaucoma surgery concluded: "Our review showed that the risk of failure of trabeculectomy at one year after surgery was lower in those participants treated with MMC compared to those treated with 5-FU." Thus, since the effectiveness of beta radiation with trabeculectomy procedures is shown to be similar to that of 5FU and 5FU is shown to have inferior effectiveness compared to MMC, the literature teaches that MMC is a more effective anti-metabolite than beta radiation.

Furthermore, a direct comparative study of intraoperative mitomycin C (MMC) and beta radiation use in pterygium surgery indicated that, "intraoperative mitomycin C is more effective than β irradiation as an adjunctive treatment for pterygium surgery using a sliding conjunctival flap," (Amano et al., 2000, British Journal of Ophthalmology 84:618-621). Thus, the prior art teaches away from use of beta radiation and instead teaches that MMC is a more effective anti-metabolite.

2. Industry expectation that mitomycin C (MMC) provides more comprehensive penetration than beta radiation:

Secondly, it is surprising to use beta radiation instead of liquid antimetabolites because the prior art teaches that liquid antimetabolites are better suited for dispersion across a wide treatment area. The importance of this wide treatment area is highlighted in the Moorfields Safe Surgery System, which was developed by Sir. Peng Khaw (Khaw et al., 2005, Glaucoma Today, March/April, 22-29). The publication that introduced the System notes that previous focal treatment with MMC led to "a thin, cystic bleb." One of the key components of the improved System is to treat "as large of an area as possible" with MMC. Critically, the publication notes: "Enlarging the surface area of treatment [with MMC] results in a more diffuse, non-cystic area, clinically. It also prevents the development of the ring of steel, which would otherwise restrict aqueous flow and promote the development of a raised, cystic, avascular bleb."

In stark contrast to the freely flowing and widely dispersed liquid antimetabolites, the use of beta radiation for ophthalmic applications has traditionally been extremely focused. Because reproducible dosage requires that the applicator be held in place for a specified period of time, the treatment area is set by the size of the applicator head. The typical diameter of an ophthalmic applicator head is only in the order of 10-14 mm and only a fraction of the head comprises the active diameter (reported to range from 4.3 to 8.9 mm) (Soares, 1995, Med. Phys. 22 (9), September, 1487-93). Even within the active diameter, the intensity of the dose falls off quickly with increasing distance from the center of the dose.

Testing of ophthalmic applicators in Soares et al. showed irregular dosage patterns and large variation between even the same model applicator. Many of the applicators did not even have the active portion aligned with the center of the applicator. Further, safety concerns led to the narrowing of the therapeutic area in ophthalmic applicators used for pterygium treatment by attaching a Castroviejo field-shaping masks. The effect of these masks is to provide a narrowed focal application like the one taught away from by the Moorfields Safe Surgery System. The Moorfields Safe Surgery System is considered to be a standard of care.

Thus, while antimetabolites such as MMC are freely flowing liquid solutions that can disperse across a wide area, treatment by beta radiation has been much more focally limited. The current teaching is that wide dispersion may be important for formation of a healthy diffuse bleb. Beta radiation does not have the ability to fluidly disperse across the tissue in the same manner as MMC. This limitation would prevent one having ordinary skill in the art from envisaging beta radiation as being able to effectively treat the wide area currently treated by permeation with liquid antimetabolites or the deep hole created in a MIMS procedure. Thus, the prior art teaches away from use of beta radiation and instead teaches that liquid anti-metabolites provide a more pervasive and desirable treatment. It is surprising to use a therapeutic approach that has long been associated with focal application, instead of an easily dispersed liquid.

3. Industry Fear that Beta Radiation is Associated with Cataracts:

Thirdly, it is surprising to use beta radiation instead of liquid antimetabolites because of a long history of reported correlation between beta radiation and cataracts. Beta radiation has been avoided in glaucoma treatment because of the widely held belief by leading ophthalmologists that beta radiation would cause cataracts. For example, a 2012 Cochrane review (Kirwan et al, 2012, Cochrane Database of Systematic Reviews Art. No. CD003433) on four trials that randomized 551 people, entitled *Beta Radiation for Glaucoma Surgery*, concluded that "people who had beta irradiation had an increased risk of cataract after surgery." As an additional example: Merriam et al concluded that the minimum cataractogenic dose for a single treatment was 200 cGy to the lens epithelium, with the probability of cataract approaching unity for a dose of 750 cGy (see Merriam G R, 1965, Trans Am Ophthalmol Soc. 54: 611-653, summarized by Kirwan et al, Eye (2003) 17, 207-215. doi:10.1038/sj.eye.6700306). The literature has made clear that the medical community teaches to avoid treatment of glaucoma with beta radiation.

In the same 2003 review on beta radiation, Kirwan also described some of the negative study reports regarding use of beta radiation in ophthalmology. The review emphasized that: "Adverse effects with beta radiation for pterygium have been widely reported. Earlier reports concentrated on lens opacity, conjunctival telangectasia, and other side effects of doses much higher than those used clinically after pterygium surgery," and that "Use of beta radiation for pterygium has diminished, with conjunctival autografting and topical mitomycin C now being widely used." Furthermore, in addition to the adverse effects noted by others, Kirwan also later reported adverse effects in his own study on the use of beta radiation for the treatment of trabeculectomy patients.

The powered, controlled and randomized study on the effect of beta radiation on success of trabeculectomy-type glaucoma surgery was published by Kirwan in 2006. Notably, the study demonstrated that, "an increased risk for cataract surgery (a known complication of trabeculectomy) in the beta radiation arm during the two years after surgery." At two years after the study the risk of developing a cataract requiring extraction was 16.7% in the radiation group and only 3.2% in the placebo group. Kirwan noted, "If beta radiation increases the need for further surgery the advantages of single therapy with trabeculectomy are much diminished."

The previously acknowledged risk and subsequent observed incidence of cataracts following the application of beta radiation was a strong discouragement against the use of beta radiation in glaucoma treatment. The randomized controlled clinical trial results revealed a notable increased incidence of cataracts associated with beta therapy; and the Kirwan authors called for an "urgent study . . . of combined surgery (trabeculectomy with beta radiation plus cataract extraction)."

Following the findings of the Kirwan study of increased cataract in the beta therapy patient group, Dhalla studied the concomitant treatment regimen of beta therapy with phacoemulsification. The Dhalla human clinical study surgically removed the patients' natural lenses at the time of beta administration. The study authors argue that this protocol is ethical even in those patients in which "if the [pre-existing] cataract does not cause significant disability it would not normally warrant surgical intervention." In other words, under normal conditions these patients would not be offered cataract surgery because the local standard of care would not warrant surgical intervention. The Dhalla beta therapy protocol included the additional surgical intervention of removing the patients' natural lens because the Kirwan study findings of increased incidence of cataract with the use of beta radiation alone.

In approving the Dhalla experimental study as ethical, the human study independent ethics committee decision provides direct authoritative teaching away from the use of beta therapy as a stand-alone adjunct to glaucoma filtration surgery.

Note that the outcome results of the Dhalla experimental human study were negative. "[The] study sample size calculation was based on detecting superiority of beta-radiation over 5FU [5 fluorouracil] which was the standard treatment . . . We detected no major difference between 5 fluorouracil and beta radiation." The disappointing study outcomes of the Dhalla study informed the medical community that beta was not superior to the antimetabolite 5FU.

The industry expectation that antimetabolites such as 5FU and MMC are more effective than beta radiation, combined with the expectation that 5FU and MMC provide more comprehensive penetration than beta radiation and the fear that beta radiation is associated with cataracts, strongly teaches away from the use of beta radiation. Thus, it would be surprising to one having ordinary skill in the art to use beta radiation with MIMS to maintain functioning drainage blebs and/or functioning drainage holes for the treatment of glaucoma.

Briefly, the present invention features methods of treating glaucoma or reducing intraocular pressure (IOP) in an eye of a patient. The method may comprise performing MIMS in the eye of the patient to form a drainage channel from an anterior chamber to allow aqueous humor to drain into a bleb in a subconjunctival space or space between a conjunctiva and Tenon's capsule; and applying a therapeutic dose of beta radiation from a radioisotope that emits beta radiation to a target area of the eye, wherein the target area is tissue surrounding a rim of the drainage channel. The method is effective for reducing an Intraocular Pressure (IOP) of the eye or treating glaucoma.

In some embodiments, the method further comprises administering a drug to the target area before, after, or both before and after applying the therapeutic amount of beta radiation to the target area. In some embodiments, the beta radiation is applied to the target area before performing MIMS, after performing MIMS, or both before and after performing MIMS. In some embodiments, the radioisotope that emits beta radiation comprises Strontium-90 (Sr-90), Phosphorus-32 (P-32), Ruthenium 106 (Ru-106), Yttrium 90 (Y-90), or a combination thereof. In some embodiments, the therapeutic dose of beta radiation at any point of the target area is within 10% of a dose of beta radiation at any other point on the target. In some embodiments, the target area further comprises at least a portion of the bleb above the drainage channel. In some embodiments, the target further comprises at least a portion of the bleb above the drainage channel and at least a portion of a perimeter of the bleb. In some embodiments, the target further comprises at least a portion of the bleb above the drainage channel, at least a portion of a perimeter of the bleb, and at least a portion of the bleb between the perimeter and the portion above the drainage channel. In some embodiments, the therapeutic dose is from 500-1000 cGy. In some embodiments, the therapeutic dose is from 450-1050 cGy.

The present invention also features a method of maintaining a functioning drainage bleb or drainage channel in an eye of a patient being treated with Minimally Invasive Micro Sclerostomy (MIMS) (the eye having a drainage channel from an anterior chamber to allow aqueous humor to drain into a bleb in a subconjunctival space or space between a conjunctiva and Tenon's capsule). In some embodiments, the method comprises applying a therapeutic dose of beta radiation from a radioisotope that emits beta radiation to a target area of the eye, wherein the target area is tissue surrounding a rim of the drainage channel. The therapeutic dose of beta radiation is effective to maintain drainage of the bleb or drainage channel.

In some embodiments, the method comprises the step of performing MIMS in the eye of the patient to form the drainage channel from an anterior chamber to allow aqueous humor to drain into a bleb in a subconjunctival space or space between a conjunctiva and Tenon's capsule. In some embodiments, the method further comprises administering a drug to the target area before, after, or both before and after applying the therapeutic amount of beta radiation to the target area.

In some embodiments, the radioisotope that emits beta radiation comprises Strontium-90 (Sr-90), Phosphorus-32 (P-32), Ruthenium 106 (Ru-106), Yttrium 90 (Y-90), or a combination thereof. In some embodiments, the therapeutic dose of beta radiation at any point of the target area is within 10% of a dose of beta radiation at any other point on the target. In some embodiments, the target area further comprises at least a portion of the bleb above the drainage channel. In some embodiments, the target further comprises at least a portion of the bleb above the drainage channel and at least a portion of a perimeter of the bleb. In some embodiments, the target further comprises at least a portion of the bleb above the drainage channel, at least a portion of a perimeter of the bleb, and at least a portion of the bleb between the perimeter and the portion above the drainage channel. In some embodiments, the therapeutic dose is from 500-1000 cGy. In some embodiments, the therapeutic dose is from 450-1050 cGy.

The present invention also features a method of inhibiting or reducing fibrogenesis and inflammation in a bleb of an eye or a drainage channel of an eye being treated with Minimally Invasive Micro Sclerostomy (MIMS) (the eye having a drainage channel from an anterior chamber to allow aqueous humor to drain into a bleb in a subconjunctival space or space between a conjunctiva and Tenon's capsule). In some embodiments, method comprises applying a therapeutic dose of beta radiation from a radioisotope that emits beta radiation to a target area of the eye, wherein the target area is tissue surrounding a rim of the drainage channel. The therapeutic dose of beta radiation causes inhibition or reduction of a fibrotic process and inflammation that otherwise leads to bleb failure or drainage channel failure.

In some embodiments, the method comprises the step of performing MIMS in the eye of the patient to form the drainage channel from an anterior chamber to allow aqueous humor to drain into a bleb in a subconjunctival space or space between a conjunctiva and Tenon's capsule. In some embodiments, the method further comprises administering a drug to the target area before, after, or both before and after applying the therapeutic amount of beta radiation to the target area.

In some embodiments, the radioisotope that emits beta radiation comprises Strontium-90 (Sr-90), Phosphorus-32 (P-32), Ruthenium 106 (Ru-106), Yttrium 90 (Y-90), or a combination thereof. In some embodiments, the therapeutic dose of beta radiation at any point of the target area is within 10% of a dose of beta radiation at any other point on the target. In some embodiments, the target area further comprises at least a portion of the bleb above the drainage channel. In some embodiments, the target further comprises at least a portion of the bleb above the drainage channel and at least a portion of a perimeter of the bleb. In some embodiments, the target further comprises at least a portion of the bleb above the drainage channel, at least a portion of a perimeter of the bleb, and at least a portion of the bleb between the perimeter and the portion above the drainage channel. In some embodiments, the therapeutic dose is from 500-1000 cGy. In some embodiments, the therapeutic dose is from 450-1050 cGy.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the office upon request and payment of the necessary fee.

The features and advantages of the present invention will become apparent from a consideration of the following detailed description presented in connection with the accompanying drawings in which:

FIG. 2A shows the MIMS apparatus. The apparatus 100 includes a hand-held probe device 110 which includes a rotatable cutting/surgical tool that cuts and removes the tissue, and a rotating motor device 120 that causes rotational movement of the cutting tool to remove the tissue the hand-held probe and the rotating motor device, being enclosed in separate housings, are interconnected by a connection assembly 140. The control unit 130 that controls the operation of the rotating motor device and the cutting tool. An optional stand 124 configured to safely hold the hand-held probe device when not being in use, and an optional pedal 134. The control unit 130 controls the operation of the motor 120 via a connection 122, which in the shown example is a wired connection. The control panel 132 includes a touch screen to select activation functions and/or parameters. The pedal is connected to the control unit via a connection 136, which in this example is a wired connection, however a wireless connection can be equally used. The pedal can be positioned inside an enclosing housing EH that minimizes accidental foot-pressing.

FIG. 2B shows on the inside, the housing of the hand-held probe encloses therein a transmission assembly configured to transmit rotational power from the rotating motor device 120 to the cutting tool 116 to thereby cause its rotation. The transmission assembly 150 includes three parts: a clutch 146, an inlet shaft 152 coupled to the clutch and an outlet shaft 154 coupled to the inlet shaft. The distal portion of the inlet shaft 152 includes an inlet gear 156 which is coupled to an outlet gear 158 formed at the proximal portion of the outlet shaft. The transmission assembly exerts both rotational and forward forces on the cutting tool 116, thus enhancing attachment of the head body, and the cutting tool, to the body organ during treatment. In the example shown, the outlet shaft 154 has certain axial lash, and the gear profile creates a force vector directed forwardly to the distal direction. After attaching the motor device to the probe device, the clutch and inlet shaft are fixedly attached as a single rigid element and turn together as one part during rotational movement.

FIG. 2C shows a schematic representing the cutting tool.

TERMS

Figure 1:
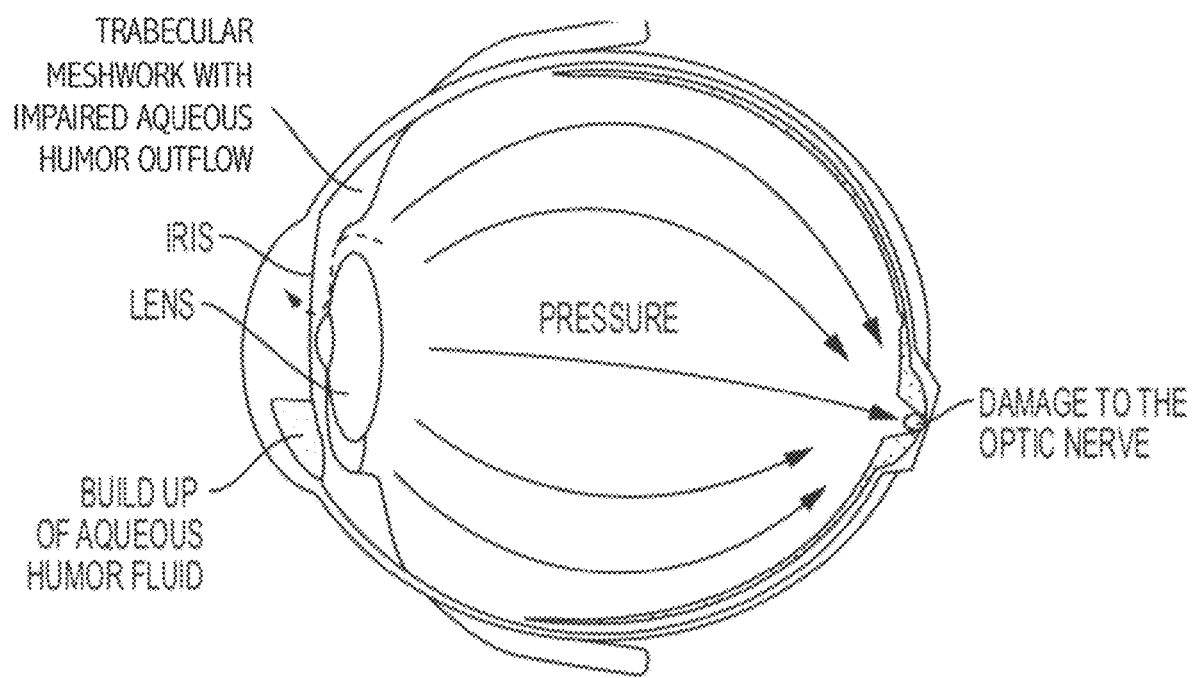
FIG. 1 shows an illustration of an eye with glaucoma.
Figure 3:
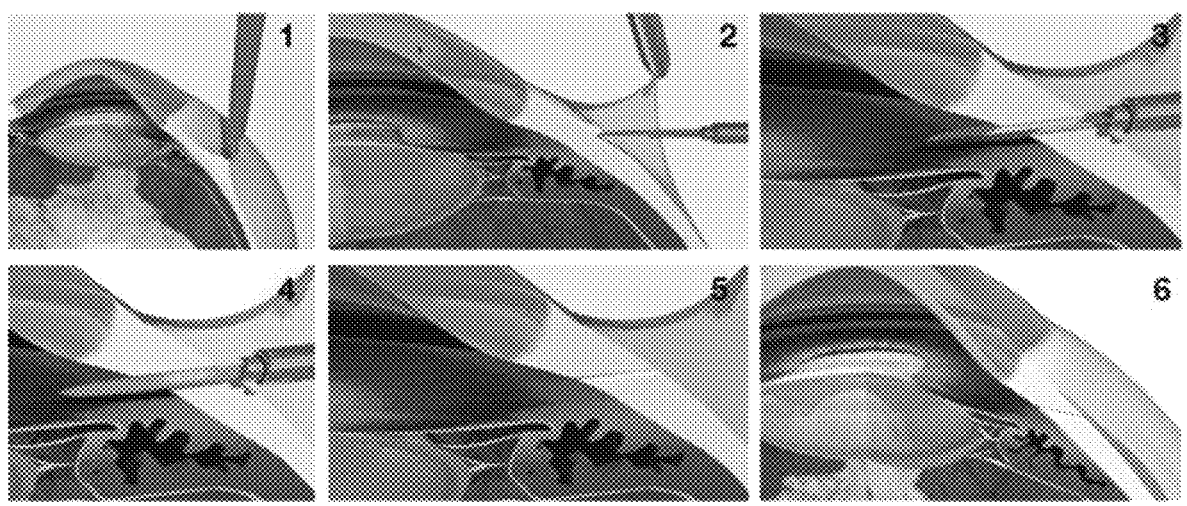
FIG. 3 shows representative images of the MIMS procedure. Panel 1 shows pulling the conjunctiva to create a "tent". Panel 2 shows that the conjunctiva is then penetrated 10-12 mm from the limbus with the MIMS device, advancing it towards the limbus. Panel 3 shows the MIMS device penetrating the limbus into the anterior chamber through the sclero-corneal junction. Panel 4 shows revolving the surgical device for sub second. Panel 5 shows a 50-100 micron diameter channel is created. Panel 6 shows that the aqueous humour is drained from the anterior chamber into the subconjuntival space. A bleb is created and the conjunctiva walls-off the bleb to provide the desired IOP.

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. The term "comprising" means that other elements can also be present in addition to the defined elements presented. The use of "comprising" indicates inclusion rather than limitation. Stated another way, the term "comprising" means "including principally, but not necessary solely". Furthermore, variation of the word "comprising", such as "comprise" and "comprises", have correspondingly the same meanings. In one respect, the technology described herein related to the herein described compositions, methods, and respective component(s) thereof, as essential to the invention, yet open to the inclusion of unspecified elements, essential or not ("comprising").

All embodiments disclosed herein can be combined with other embodiments unless the context clearly dictates otherwise.

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references Dosimetry techniques include film dosimetry. In one example the RBS is applied to radiographic film, for example Gafchromic™ film. The dose at various depths can also be measured by placing an intervening material, such as Plastic Water™, of known thicknesses between the RBS and the film. A transmission densitometer in conjunction with a film optical density vs. dose chart, allows for the film opacity to be measured and then converted to delivered dose. Other methods include Thermoluminescent methods (TLD chips). TLD chips are small plastic chips with millimeter dimensions having a crystal lattice that absorbs ionizing radiation.

Dose variation is described as that across the diameter assuming a central point maximum dose. However, in practice it has been demonstrated that the maximum dose may be off center. Thus, a description of variation of dose across the diameter may also include the variation of dose over the area, and though the depth.

In general use in the profession of ophthalmology the term "conjunctivae" may refer to the conjunctivae in combination with the Tenon's capsule. Also, in general use in the profession of ophthalmology the term "conjunctivae" may refer to the conjunctivae alone, not including the Tenon's capsule. References herein to "conjunctivae" can include either and/or both meanings.

It is customary in beta surface applicators to specify the superficial dose at the depth equal to half the thickness of the film, generally about 0.2 mm for some Gafchromic™ films. Other specifications for dose at a specific depth can also be used. The Planning Treatment Volume (defined herein) can include the entire thickness of the conjunctivae and membranes overlaying the sclera; as also described herein, these depths typically range from about 0.194 mm to about 0.573 mm.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

Beam Modification: Desirable modification in the spatial distribution of radiation (e.g., within the patient) by insertion of any material in the beam path. Beam modification increases conformity allowing a higher dose delivery to the target, while sparing more of normal tissue simultaneously.

There are four main types of beam modification: (1) Shielding: To eliminate radiation dose to some special parts of the zone at which the beam is directed. In general use is the fabrication of low-melting-temperature alloy (Lipowitz metal or Cerroblend) shielding blocks that are custom made for the individual patient and used to shield normal tissue and critical organs. For example, during total body irradiation (TBI), customized shielding blocks are positioned in front of the lungs to reduce radiation dose. (2) Compensation: To allow normal dose distribution data to be applied to the treated zone, when the beam enters obliquely through the body, or where different types of tissues are present. (3) Wedge filtration: Where a special tilt in isodose curves is obtained. (4) Flattening: Where the spatial distribution of the natural beam is altered by reducing the central exposure rate relative to the peripheral. In general use is a beam flattening filter that reduces the central exposure rate relative to that near the edge of the beam. This technique is used for linear accelerators. The filter is designed so that the thickest part is in the center. These are often constructed of copper or brass.

Innovations such as stereotaxic radiotherapy, intensity modulated radiation therapy, and conformal radiotherapy are also applied towards the goal of sparing normal tissue and critical organs. For example, Linear Accelerators designed with Multileaf Collimators have, in many circumstances, replaced shielding bocks.

Brachytherapy (see also Radionuclide Brachytherapy Source (RBS)): According to the American Association of Physicists in Medicine (AAPM), brachytherapy is "the clinical use of small encapsulated radioactive sources at a short distance from the target volume for irradiation of malignant tumors or nonmalignant lesions." Generally, in medical practice, brachytherapy can be categorized as topical or plaque brachytherapy, intracavitary, and interstitial.

Some implementations of brachytherapy employ permanently implanted Radionuclide Brachytherapy Sources (RBSs). For example, in Low Dose Rate (LDR) brachytherapy for prostate cancer, a standard of care treatment, radioactive Iodine-125 RBSs are placed directly into the prostate where they remain indefinitely. In another implementation, High Dose Rate (HDR) brachytherapy TheraSpheres are infused into the arteries that feed liver tumors. These microspheres then embolize, lodging themselves in the liver's capillaries and bathing the malignancy in high levels of yttrium-90 radiation. In both these implementations, the total dose is given by consuming the entire radioisotope. Some other implementations of brachytherapy employ a transient placement of the RBS. For example, in after-loaded High Dose Rate (HDR) brachytherapy, very tiny plastic catheters are placed into the prostate gland, and a series of radiation treatments is given through these catheters. A computer-controlled machine pushes a single highly radioactive iridium-192 RBS into the catheters one by one for a specified dwell time at locations throughout the volume being irradiated. The catheters are then easily pulled out, and no radioactive material is left at the prostate gland. Another example of transient placement of an RBS includes prophylactic therapy for restenosis of coronary arteries after stent implantation. This is a non-malignant condition that has been successfully treated by placing a catheter into the coronary artery, then inserting a HDR radioactive source into the catheter and holding it there for a predetermined time in order to deliver a sufficient dose to the vessel wall.

Drainage Device or Drainage System: Any or a combination of the general and specific approaches for draining aqueous humor, such as the therapeutic and devices described herein, e.g., minimally invasive glaucoma surgery (MIGS) devices and surgery, Minimally Invasive Micro Sclerostomy (MIMS) devices and surgery, trabeculectomy surgery, sclerostomy, etc., that are employed to reduce intraocular pressure (IOP) by means of surgical intervention with or without a device.

Flow Controlled Stents (see also Minimally Invasive Glaucoma Surgery (MIGS)): Some MIGS-associated devices control flow of the aqueous humor. For example, the XEN® gel stent (Allergan) is a gelatin and glutaraldehyde tube, which is preloaded in a disposable injector and implanted using an ab interno approach. The surgeon inserts the injector through a clear cornea incision and tunnels through the sclera at or anterior to Schlemm's canal to deploy the distal portion of the stent within the subconjunctival space. This creates a pathway for aqueous to flow from the anterior chamber to the subconjunctival space, forming a bleb. Another flow-controlled stent is the InnFocus MicroShunt® (InnFocus, Santen). The surgeon inserts this device into the anterior chamber through an ab externo approach, creating a bleb in the subconjunctival space.

Functioning Drainage Bleb: A bleb that is effective for draining aqueous humor from the eye to reduce intraocular pressure (IOP) of the eye to an appropriate level.

Early bleb grading systems included those proposed by Kronfeld (1969), Migdal and Hitchings (1983), and Picht and Grehn (1998). Subsequent bleb grading systems identified and incorporated a graded assessment of various bleb parameters such as vascularity, height, width, microcystic changes, encystment and diffuse/demarcated zones.

There are two recently described grading systems for clinical grading of filtering surgery blebs: the Moorfields Bleb Grading System (MBGS) and the Indiana Bleb Appearance Grading Scale (IBAGS). The MBGS built upon the system used for this tele-medicine study and expanded it to include an assessment of vascularity away from the center of the bleb and a way to represent mixed-morphology blebs. In this scheme, central area (1-5), maximal area (1-5), bleb height (1-4) and subconjunctival blood (0-1) were assessed.

In addition, three areas of the bleb were graded separately for vascularity, including bleb center conjunctiva, peripheral conjunctiva and non-bleb conjunctiva. Vascularity in each area was assigned a score from 1 to 5. A study found good inter-observer agreement and clinical reproducibility in the IBAGS and MBGS (Wells A P, Ashraff N N, Hall R C, et al. Comparison of two clinical bleb grading systems. Ophthalmology 2006; 113:77-83.)

The Moorfields bleb grading system was developed as the importance of bleb appearance to outcome was realized. Blebs that develop thin avascular zones are at increased risk of leakage and late hypotony as well as sight threatening bleb related infections.

The Indiana Bleb Appearance Grading Scale is a system for classifying the morphologic slit lamp appearance of filtration blebs. The Indiana Bleb Appearance Grading Scale contains a set of photographic standards illustrating a range of filtering bleb morphology selected from the slide library of the Glaucoma Service at the Indiana University Department of Ophthalmology. These standards consist of slit lamp images for grading bleb height, extent, vascularity, and leakage with the Seidel test. For grading, the morphologic appearance of the filtration bleb is assessed relative to the standard images for the 4 parameters and scored accordingly.

For reference, a failed or failing bleb may have "restricted posterior flow with the so-called 'ring of steel'," e.g., a ring of scar tissue or fibrosis adhering the conjunctiva to the sclera at the periphery of the bleb that restricts the flow of aqueous humor (see Dhingra S, Khaw P T. The Moorfields Safer Surgery System. Middle East African Journal of Ophthalmology. 2009; 16(3):112-115). Other attributes of failed or failing blebs may include cystic appearance and/or changes in vascularization and/or scar tissue and/or thinning of the conjunctiva overlaying the bleb and/or a tense bleb and/or other observable or measurable changes as may be included in either the Indiana Bleb Appearance Grading Scale or Moorfields Bleb Grading System. Other functional determinates of failed or failing blebs or glaucoma surgery may include increased IOP, or IOP that has not decreased sufficiently.

Minimally Invasive Glaucoma Surgery (MIGS): MIGS is a recent innovation in the surgical treatment of glaucoma developed to minimize the complications from tubes and trabeculectomy. MIGS is a term applied to the widening range of implants, devices, and techniques that seek to lower intraocular pressure with less surgical risk than the more established procedures. In most cases, conjunctiva-involving devices require a subconjunctival bleb to receive the fluid and allow for its extraocular resorption. Flow-controlled conjunctiva-involving devices typically attempt to control flow and lower IOP to normal pressure and also minimizing hypotony (too low pressure in the eye) by applying Poiseuille's law of laminar flow to create a tube that is sufficiently long and narrow to restrict and control outflow. Some MIGS devices include Flow Controlled Stents, microshunts to Shlemm's Canal, Suprachoroidal Devices, and devices for Trabeculotomy. Examples of microshunts to Shlemm's Canal include iStent® (Glaukos®) and Hydrus™ (Ivantis). Examples of suprachoroidal devices include CyPass® (Alcon), Solx® gold shunt (Solx), and iStent Supra® (Glaukos). An example of a trabeculotomy device includes the Trabectome® (NeoMedix) electrocautery device.

Minimally Invasive Micro Sclerostomy (MIMS) or Sclerostomy: Sclerostomy is a procedure in which the surgeon makes a small opening in the sclera to reduce intraocular pressure (IOP), usually in patients with open-angle glaucoma. It is classified as a type of glaucoma filtering surgery. Minimally invasive micro sclerostomy (MIMS, Sanoculis) is a recent innovative technique that combines the mechanism of conventional trabeculectomy and simple needling. In the course of the surgery, a sclero-corneal drainage channel is created. The MIMS procedure can be performed ab externo by creating a sclero-corneal channel to drain the aqueous humor from the anterior chamber to the subconjunctival space. The channel created with MIMS is designed to obtain a controlled fluid flow. Laser sclerostomy can be performed in a less invasive manner than standard filtering surgery. Other studies have explored the use of laser energy of varying wavelengths, properties, and tissue interaction to create thermal sclerostomies. Several methods deliver laser energy by mirrored contact lenses to the internal face of the filtration angle or by fiberoptic cables for ab interno or ab externo sclerostomy formation.

Planning Treatment Volume or Planning Target Volume (PTV): A volume that encloses all the tissue intended for irradiation. Beta sources project radiation filling the adjacent volume of space. The dose at any point within this volume of tissue is generally not uniform. An adequate description of the dosimetry is the PTV and generally also includes the doses outside the PTV that effect other, non-target, tissue. It has been the history of radiation oncology that delivery of radiation that best matches the PTV while limiting dose outside of the target tissue leads to improved clinical response rates.

Radioactive isotope, radionuclide, radioisotope: An element that has an unstable nucleus and emits radiation during its decay to a stable form. There may be several steps in the decay from a radioactive to a stable nucleus. There are four types of radioactive decay: alpha, beta negative, beta positive, and electron capture. Gamma rays can be emitted by the daughter nucleus in a de-excitation following the decay process. These emissions are considered ionizing radiation because they are powerful enough to liberate an electron from another atom.

Therapeutic radionuclides can occur naturally or can be artificially produced, for example by nuclear reactors or particle accelerators. Radionuclide generators are used to separate daughter isotopes from parent isotopes following natural decay.

Non-limiting examples of radioactive isotopes following one of the four decay processes are given herein: (1) Alpha decay: radium 226, americium 241; (2) Beta minus: iridium 192, cesium 137, phosphorous 32 (P-32), strontium 90 (Sr-90), yttrium 90 (Y-90), ruthenium 106, rhodium-106; (3) Beta positive: fluorine 18; (4) Electron capture: iodine 125, palladium 106. Examples of gamma emission include iridium 192 and cesium 137.

Half-life is defined as the time it takes for one-half of the atoms of a radioactive material to disintegrate. Half-lives for various radioisotopes can range from a few microseconds to billions of years.

The term activity in the radioactive-decay processes refers to the number of disintegrations per second. The units of measure for activity in a given source are the curie (Ci) and becquerel (Bq). One (1) Becquerel (Bq) is one disintegration per second.

An older unit is the Curie (Ci), wherein one (1) Ci is $3.7 \times 10^{10}$ Bq.

Radionuclide Brachytherapy Source (RBS) (see also Brachytherapy): According to the US Federal Code of Regulations, a Radionuclide Brachytherapy Source (RBS) is "a device that consists of a radionuclide what may be enclosed in a sealed container made of gold, titanium, stainless steel, or platinum and intended for medical purposes to be placed onto a body surface or into a body cavity or tissue as a source of nuclear radiation for therapy." Other forms of brachytherapy sources are also used in practice. For example, a commercially available conformal source is a flexible, thin film made of a polymer chemically bound to Phosphorous-32 (P-32). Another product is the TheraSphere, a radiotherapy treatment for hepatocellular carcinoma (HCC) that consists of millions of microscopic, radioactive glass microspheres (20-30 micrometers in diameter) containing Yttrium-90. Other forms of brachytherapy employ x-ray generators as sources instead of radioisotopes.

Trabeculectomy: A procedure wherein a small hole is made in the sclera and is covered by a thin trap-door. Aqueous humor drains through the trap door to a bleb. As an example, in some trabeculectomy procedures, an initial pocket is created under the conjunctiva and Tenon's capsule and the wound bed is treated with mitomycin C soaked sponges using a "fornix-based" conjunctival incision at the corneoscleral junction. A partial thickness scleral flap with its base at the corneoscleral junction after cauterization of the flap area is created. Further, a window opening is created under the flap with a Kelly-punch or a Khaw Descemet Membrane Punch to remove a portion of the sclera, Schlemm's canal, and the trabecular meshwork to enter the anterior chamber. An iridectomy is done in many cases to prevent future blockage of the sclerostomy. The scleral flap is then sutured loosely back in place with several sutures. The conjunctiva is closed in a watertight fashion at the end of the procedure.

Trans-scleral Drainage Devices: Devices that shunt aqueous humor from the anterior chamber to a subconjunctival reservoir. As an example, the EX-PRESS® Glaucoma Filtration Device channels aqueous humor through a secure lumen to a half-thickness scleral flap, creating a subconjunctival filtration bleb. The device's lumen provides a standardized opening for aqueous humor flow while also providing some resistance, which appears to add further stability to the anterior chamber during surgery and the early post-op period.

Treat, Treatment, Treating: These terms refer to both therapeutic treatment, e.g., elimination of a disease, disorder, or condition, and prophylactic or preventative measures, e.g., preventing or slowing the development of a disease or condition, reducing at least one adverse effect or symptom of a disease, condition, or disorder, etc. Treatment may be "effective" if one or more symptoms or clinical markers are reduced as that term is defined herein. Alternatively, a treatment may be "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom (s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a particular disease, disorder, or condition, as well as those likely to develop a particular disease, disorder, or condition due to genetic susceptibility or other factors.

Valves: Devices that can be used for glaucoma treatment, wherein instead of using a natural bleb, these devices use a synthetic reservoir (or plate), which is implanted under the conjunctiva to allow flow of aqueous fluid. Valve devices include the Baerveldt® implant (Pharmacia Co.), the Ahmed® glaucoma valve (New World Medical), the Krupin-Denver eye valve to disc implant (E. Benson Hood Laboratories), and the Molteno® and Molteno3® drainage devices (Molteno® Ophthalmic Ltd.).

Description of Preferred Embodiments

Referring now to FIGS. 1-15, the present invention provides methods and systems for maintaining a functioning drainage bleb, wherein the methods and systems feature a Minimally Invasive Micro Sclerostomy (MIMS) procedure and the application of beta radiation to the drainage bleb, the drainage channel, or a combination thereof.

Isotopes and Radioactivity

The US Nuclear Regulatory Commission (USNRC) defines radioactivity as "the amount of ionizing radiation released by a material. Whether it emits alpha or beta particles, gamma rays, x-rays, or neutrons, a quantity of radioactive material is expressed in terms of its radioactivity (or simply its activity), which represents how many atoms in the material decay in a given time period. The units of measure for radioactivity are the curie (Ci) and becquerel (Bq)." Activity in a radioactive-decay process is defined as the number of disintegrations per second, or the number of unstable atomic nuclei that decay per second in a given sample. Activity is expressed in the International System of Units by the becquerel (abbreviated Bq), which is exactly equal to one disintegration per second. Another unit that may be used is the Curie, wherein one curie is approximately the activity of 1 gram of radium and equals (exactly) $3.7 \times 10^{10}$ becquerel. The specific activity of radionuclides is relevant when it comes to select them for production for therapeutic pharmaceuticals.

By the USNRC definition, absorbed dose is defined as the amount of radiation absorbed, e.g., the amount of energy that radioactive sources deposit in materials through which they pass or the concentration of energy deposited in tissue as a result of an exposure to ionizing radiation. The absorbed dose is equal to the radiation exposure (ions or Ci/kg) of the radiation beam multiplied by the ionization energy of the medium to be ionized. Typically, the units for absorbed dose are the radiation absorbed dose (rad) and gray (Gy). Gy is a unit of ionizing radiation dose defined as the absorption of one joule of radiation energy per kilogram of matter. The rad has generally been replaced by the Gy in SI derived units. 1 Gy is equivalent to 100 rad.

Radionuclide generators are devices that produce a useful short-lived medical radionuclide (known as "daughter" products) from the radioactive transformation of a long-lived radionuclide (called a "parent"). By having a supply of parent on hand at a facility, the daughter is continually generated on site. The generator permits ready separation of the daughter radionuclide from the parent. One of the most widely used generator devices (often referred as a "cow") is the technetium 99 generator. It allows the extraction of the metastable isotope 99mTc of technetium from a source of decaying molybdenum-99. 99Mo has a half-life of 66 hours and can be easily transported over long distances to hospitals where its decay product technetium-99m (with a half-life of only 6 hours, inconvenient for transport) is extracted and used for a variety of nuclear medicine procedures, where its short half-life is very useful.

Generators can also be constructed for supply of other daughter radioisotopes. Ruthenium 106 (Ru-106) is a commercially available radioisotope with a half-life of 668373 days, making it a good candidate for a parent isotope in a cow or generator. The decay of Ru-106 to rhodium-106 (Rh-106) produces only a low energy beta of 39 Kev that is not useful for therapy. However, Rh-106 has an energetic beta decay useful for brachytherapy: Rh-106 has a half-life of 30 seconds and decays by beta emission to palladium 106 (Pd-106) with a maximum decay energy of 3.541 Mev and an average energy of 96.9 Kev. As an example, in some embodiments, the present invention features a device loaded from a Ruthenium-106 cow with an activity of rhodium-106 providing for the full prescribed dose. The device can be applied to the target volume to deliver the full activity of its contents. For example, the device may be placed over the target lesion for 10 half-lives (300 seconds), delivering all its radioactive energy and consuming the rhodium-106, depleting it to palladium.

In some embodiments, the present invention features the use of Ru-106 in secular equilibrium with Rh-106. Ru-106 decays by beta radiation to Rh-106. The two isotopes are in secular equilibrium with the decay rate of the combined source controlled by the Ru-106 parent but with the therapeutic beta radiations emanating from the daughter Rh-106.

Yttrium-90 is commercially available from Strontium-90 cows. As another example, in some embodiments, the present invention features the use of Yttrium-90 with a half-life of 64 hours. Y-90 decays to Zirconium 90 (Zr-90), a stable isotope, along three different routes via beta emission, wherein 99.985% of the time it decays with a maximum beta particle energy of 2.2801 MeV and a mean beta particle energy of 0.9337 MeV, or approximately or $1.5 \times 10{-13}$ joules. The other minor decay paths produce additional low energy gamma-rays, and electrons. Compared to the dominant path, the radiation doses from these paths are clinically negligible.

Currently, strontium-90 is also commercially available. As another example, in some embodiments, the present invention features the use of Strontium 90 (Sr-90) in secular equilibrium with Yttrium 90 (Y-90). Strontium 90 (Sr-90) decays by beta radiation to Yttrium 90 (Y-90). The parent Sr-90 isotope has a half-life of 28.79 years. The daughter Y-90 isotope has a half-life of 64.0 hours. The two isotopes are in secular equilibrium with the decay rate of the combined source controlled by the Sr-90 parent but with the therapeutic beta radiations emanating from the daughter Y-90 with maximum energy of 2.28 MeV and an average energy of 934 keV.

The Planning Target Volume (PTV) or Planning Treatment Volume (PTV) is a geometrical concept introduced for radiation treatment planning. The PTV is used to ensure that the prescribed dose is actually delivered to all parts of the target tissue. Without limiting the invention to any particular surgical practice, a medical journal article details the surgical creation of the bleb in which "the surgeon dissects backward with Westcott scissors to make a pocket approximately 10 to 15 mm posteriorly and sufficiently wide to accommodate the antimetabolite sponges". In this example, the surgeon opened the potential space under the conjunctiva and Tenon's capsule creating an approximately 10 to 15 mm diameter bleb site. As an example, it would follow that the Target Volume could be defined as a disk of diameter 15 mm and depth of 0.3 mm, containing the conjunctiva and Tenon's capsule tissue.

For example, a prescription dose of brachytherapy of 10 Gray (1000cGy) is 10 joules/kg absorbed dose throughout the Target Volume. Measurements have suggested a model Sr-90/Y-90 RBS with Activity of 1.48 GBq produces a surface dose rate of approximately 0.20 Gy per second. To deliver a dose of 10 Gy to the Target Volume would require an irradiation time of 50 seconds. The number nuclei that decay during this 50 second treatment would be $1.48 \times 10^9$ Bq (disintegrations per second)$\times 50$ seconds=$7.4 \times 10^{10}$.

Biological Effects of Radiation

The biological effectiveness of radiation depends on the linear energy transfer (LET), total dose, fractionation rate, and radiosensitivity of the targeted cells or tissues. As radiation interacts with matter, it loses its energy through interactions with atoms in its direct path. In radiation therapy, LET is defined as the average amount of energy lost per defined distance in tissue, as in the energy deposited into a handful of cells. LET occurs at different rates in different tissues, and quantification of LET in cellular systems is an important component of determining correct dosage in radiology. Low LET radiations are X-rays, gamma rays and beta particles.

Radiation induced ionizations can act directly on the cellular molecules and cause damage, such as DNA damage. Radiation induced ionizations also can act indirectly, producing free radicals that are derived from the ionization or excitation of the water component of the cell. Exposure of cells to ionizing radiation induces high-energy radiolysis of $H_2O$ water molecules into H+ and OH− radicals. These radicals are themselves chemically reactive, and in turn recombine to produce a series of highly reactive combinations such as superoxide ($O_2^-$) and peroxide ($H_2O_2$) that produce oxidative damage to molecules, such as DNA, within the cell. Ionizing radiation-induced DNA breaks represent one of the dominant mechanisms of action of beta brachytherapy.

Multiple pathways are involved in the cell after its exposure to ionizing radiation. In the cellular response to radiation, several sensors detect the induced DNA damage and trigger signal transduction pathways. The activation of several signal transduction pathways by ionizing radiation results in altered expression of a series of target genes.

The promoters or enhancers of these genes may contain binding sites for one or more transcription factors, and a specific transcription factor can influence the transcription of multiple genes. The transcription factors p53, nuclear factor κB (NF-κB), the specificity protein 1 (SP1)-related retinoblastoma control proteins (RCPs), two p53dependent genes, GADD45 and CDKN1A, and genes associated with the NER pathway (e.g., XPC) are typically upregulated by ionizing radiation exposure. Interestingly, NF-κ B activation has been shown to strongly depend on charged particles' LET, with a maximal activation in the LET range of 90-300 keV/μm.

Importantly, the transcribed subset of target genes is critical for the decision between resuming normal function after cell-cycle arrest and DNA repair, entering senescence, or proceeding through apoptosis in cases of severe DNA damage.

Arrest of the cell cycle is an important part of DNA damage response, facilitating DNA repair and maintenance of genomic stability. Regulators of cell cycle arrest are activated by phosphorylation by ataxia telangiectasia mutated (ATM) and ATR. For example, p53 has a short half-life and is stabilized in response to a variety of cellular stresses after phosphorylation by ATM. After exposure to ionizing radiation, phosphorylation of the serine residues 15 and 20 on p53 by checkpoint kinase 2 (CHK2) reduces its binding to MDM2, which in its bound state targets p53 for degradation by the proteasome pathway. Thus, dissociation of p53 from MDM2 prolongs the half-life of p53. Other proteins, such as Pin 1, Parc, and p300, and p300/CBP-associated factor (PCAF) histone acetyltransferases regulate the transactivation activity of p53. For efficient repair, especially in non-dividing cells, cellular levels of deoxyribonucleotides are increased during the DNA damage repair by p53-dependent transcriptional induction of the ribonucleotide reductase RRM2B (p53R2). It is accepted that the severity of DNA damage is the critical factor in directing the signaling cascade toward reversible cell cycle arrest or apoptosis. As part of the signaling cascade, the abundance of p53 protein, specific posttranslational modifications, and its interaction with downstream effectors, such as GADD45α or p21, may be responsible for directing the cellular response at this decision point.

Other pathways besides DNA and p53 can be involved in the cellular response to exposure to ionizing radiation. For example, ionizing radiation can produce reactive oxygen species (ROS) in the cytoplasm.

Low-dose radiotherapy (LD-RT) is known to exert an anti-inflammatory effect. In vitro models have revealed anti-inflammatory effects of LD-RT in doses ranging from 0.1-1.0 Gy on immune cells such as macrophages and neutrophils. Studies have also shown that low-dose radiation therapy has an anti-inflammatory effect involving diminished CCL20 chemokine expression and granulocyte/endothelial cell adhesion. An in vitro study by Khaw et al. (1991, British Journal of Ophthalmology 75:580-583) of beta irradiation of fibroblasts in culture found that "radiation reduces the proliferation of human Tenon's capsule fibroblasts. The doses of radiation which inhibited cell proliferation more than 50% (at day 7 and 14) and yet did not cause a decrease in the cell population were 500, 750, and 1000 rads." The fibroblasts enter a period of growth arrest but do not die.

The present invention features systems and devices for the application of beta radiation used in combination with surgical procedures and/or implants (e.g., MIGS implants) as described herein. The brachytherapy provided by the systems and devices herein helps to prevent or reduce bleb scarring or failure to maintain a functioning bleb. Without wishing to limit the present invention to any theory or mechanism, it is believed that the brachytherapy devices and systems herein may help to inhibit or reduce inflammation and/or fibrogenesis by downregulating cellular (e.g., fibroblast) activity without cell death.

The application of beta radiation provides a medicament-like treatment, similar to a drug, wherein the beta radiation, when consumed by the cells, causes biological changes in signaling and gene transcription, thereby affecting cellular activity and growth, e.g., cell cycle arrest.

The present invention provides compositions or products that are radioactive compositions (sources of beta radiation). The radioactive composition has a therapeutic effect via the generation of beta radiation by, for example, the mechanisms previously discussed. In generating the beta radiation, radioactive composition is consumed (e.g., the product is gradually used up), in that the radioisotope atoms of the beta radioisotope brachytherapy source decay into other nuclides.

Targets of the Eye

As previously discussed, the present invention provides systems and devices, e.g., ophthalmic applicator systems, brachytherapy systems, etc., for applying beta radiation, e.g., to a treatment area or target of the eye.

The target may be an area of tissue surrounding the rim of the drainage channel, e.g., tissue within a certain distance from the center of the drainage hole. For example, in some embodiments, the target is tissue within 2 mm from the center of the drainage hole. In some embodiments, the target is tissue within 3 mm from the center of the drainage hole. In some embodiments, the target is tissue within 4 mm from the center of the drainage hole. In some embodiments, the target is tissue within 5 mm from the center of the drainage hole. In some embodiments, the target is tissue within 6 mm from the center of the drainage hole. In some embodiments, the target is tissue within 7 mm from the center of the drainage hole. In some embodiments, the target is tissue within 8 mm from the center of the drainage hole.

The target may be a portion of the bleb above the drainage channel. In some embodiments, the target is an area of the bleb above the drainage channel that extends within 2 mm from the center of the drainage hole. In some embodiments, the target is an area of the bleb above the drainage channel that extends within 3 mm from the center of the drainage hole. In some embodiments, the target is an area of the bleb above the drainage channel that extends within 4 mm from the center of the drainage hole. In some embodiments, the target is an area of the bleb above the drainage channel that extends within 5 mm from the center of the drainage hole. In some embodiments, the target is an area of the bleb above the drainage channel that extends within 6 mm from the center of the drainage hole. In some embodiments, the target is an area of the bleb above the drainage channel that extends within 7 mm from the center of the drainage hole. In some embodiments, the target is an area of the bleb above the drainage channel that extends within 8 mm from the center of the drainage hole.

In some embodiments, the target is a target other than that associated with MIGS/MIMS/trabeculectomy. In some embodiments, the ophthalmic target is other targets than those associated with glaucoma drainage surgery. In some embodiments the target is inflammation, autoimmune mediated pathologies, or vascular pathologies of the eye. In some embodiments, the target is associated with infections (for example, Herpes Simplex Keratitis or Tuberculous sclerokeratitis), Corneal ulcerations (for example, Moorens), Allergic disorders (for example, Vernal), benign or malignant Tumors (for example, Squamous Cell Carcinoma) or benign growths (for example, papillomas), Degenerations (for example, pterygium), Cicitarising disease (for example, pemphigoid), Inflammations (for example, meibomian gland), ocular manifestations of Stevens-Johnson syndrome, Drug-induced cicatrizing conjunctivitis, Ligneous conjunctivitis, Corneal Vascularization, Pterygia, Vernal Catarrh, Small papillomas of the eyelid, limbal carcinoma, ocular malignant melanoma, nevus pigmentosus of the conjunctiva, hemangioma, chalazion. In some embodiments, the target is in the orbit of the eye. The present invention includes other ophthalmic indications and is not limited to the aforementioned targets.

Brachytherapy Systems and Devices

The brachytherapy systems and devices of the present invention comprise: a radionuclide brachytherapy source (RBS) for supplying the radiation that is delivered to the target, and a brachytherapy applicator.

(A) Radionuclide Brachytherapy Source (RBS)

The RBS of the present invention is constructed in a manner that is consistent with the Federal Code of Regulations, but is not limited to the terms mentioned in the Code. For example, the RBS of the present invention may further comprise a substrate. Also, for example, in addition to being enclosed by the mentioned "gold, titanium, stainless steel, or platinum", in some embodiments the radionuclide (isotope)

of the present invention may be enclosed by a combination of one or more of "gold, titanium, stainless steel, or platinum". In some embodiments, the radionuclide (isotope) of the present invention may be enclosed by one or more layers of an inert material comprising silver, gold, titanium, stainless steel, platinum, tin, zinc, nickel, copper, other metals, ceramics, glass, or a combination of these.

In some embodiments, the RBS comprises a substrate, a radioactive isotope (e.g., Sr-90, Y-90, Rh-106, P-32, etc.), and an encapsulation. In some embodiments, the isotope is coated on the substrate, and both the substrate and isotope are further coated with the encapsulation. In some embodiments, the radioactive isotope is embedded in the substrate. In some embodiments, the radioactive isotope is part of the substrate matrix. In some embodiments, the encapsulation may be coated onto the isotope, and optionally, a portion of the substrate. In some embodiments, the encapsulation is coated around the entire substrate and the isotope. In some embodiments, the encapsulation encloses the isotope. In some embodiments, the encapsulation encloses the entire substrate and the isotope. In some embodiments, the radioactive isotope is an independent piece and is sandwiched between the encapsulation and the substrate.

In some embodiments, a surface on the substrate is shaped in a manner to provide a controlled projection of radiation. The substrate may be constructed from a variety of materials. For example, in some embodiments the substrate is constructed from a material comprising, a silver, an aluminum, a stainless steel, tungsten, nickel, tin, zirconium, zinc, copper, a metallic material, a ceramic material, a ceramic matrix, the like, or a combination thereof. In some embodiments, the substrate functions to shield a portion of the radiation emitted from the isotope. The encapsulation may be constructed from a variety of materials, for example from one or more layers of an inert material comprising a steel, a silver, a gold, a titanium, a platinum, another bio-compatible material, the like, or a combination thereof.

The radionuclide brachytherapy source (RBS) is constructed to provide a substantially uniform radiation dose across the target. For example, previous radiation applicators may only treat the center part of the target or under-dose the peripheral area and/or overdose the center. The present invention may provide a more uniform dose across the target area (e.g., see FIG. 4). However, the present invention is not limited to the dosimetry described herein.

In some embodiments, the RBS is designed such that the dose received at the perimeter of the bleb is higher than that received at the center of the bleb.

In some embodiments, the RBS is designed such that the dose received at the perimeter of the bleb is similar to that at the center, e.g., not less than 80% of the dose of the center, not less than 90% of the dose at the center, etc. In some embodiments, the RBS is designed such that any point of the target is within 20% of the dose of any other point of the target, e.g., the variation of dose across the target is not more than 20%, e.g., at any given point the variation is not more than 20%. In some embodiments, the RBS is designed such that any point of the target is within 15% of the dose of any other point of the target, e.g., the variation of dose across the target is not more than 15%, e.g., at any given point the variation is not more than 15%. In some embodiments, the RBS is designed such that any point of the target is within 10% of the dose of any other point of the target, e.g., the variation of dose across the target is not more than 10%, e.g., at any given point the variation is not more than 10%. In some embodiments, the RBS is designed such that any point of the target is within 8% of the dose of any other point of the target, e.g., the variation of dose across the target is not more than 8%, e.g., at any given point the variation is not more than 8%. In some embodiments, the RBS is designed such that any point of the target is within 5% of the dose of any other point of the target, e.g., the variation of dose across the target is not more than 5%, e.g., at any given point the variation is not more than 5%. In some embodiments, the RBS is designed such that any point of the target is within 3% of the dose of any other point of the target, e.g., the variation of dose across the target is not more than 3%, e.g., at any given point the variation is not more than 3%.

With respect to the aforementioned dose profiles, because in some embodiments the target area, and Planning Treatment Volume, has a small depth (e.g., 0.3 mm), e.g., in the case of treating some blebs, the doses cited may refer to the doses adjacent to the surface of the device, for example at a depth of 0.15 mm. In other embodiments, the doses cited may refer to the doses at a depth of 0.05, 0.1, 0.2, 0.25, 0.3, 0.35, 0.4, 0.45, or 0.5 mm. For example, in some embodiments, the target area includes a hole associated with MIMS, and the depth of the target area is greater than that would be expected of a target associated with a bleb.

Iterative computer simulations of output dosimetry may be used to determine an optimized design of device. Film dosimetry is a method of measuring radioactive delivery from a source and can be used to measure the dose across the target. It can also be used to calibrate or compare radioactive sources or to determine the homogeneity of the dose pattern.

The RBS may be disc shaped or have an annulus or rounded shape; however, the present invention is not limited to those shapes, and any shape that achieves a desired dose profile is encompassed herein. The shape of the RBS may help provide a controlled projection of radiation (e.g., a therapeutic dose) onto the target. The shape of the RBS may help the radiation dose to fall off quickly at the periphery of the target (whatever the target is determined to be, e.g., the whole bleb, a portion of the bleb, etc.). This may help keep the radiation within a limited area/volume and may help prevent unwanted exposure of structures such as the lens to radiation.

In some embodiments, the RBS has a diameter from 4 to 20 mm. In some embodiments, the RBS has a diameter from 5 to 15 mm. In some embodiments, the RBS has a diameter from 10 to 20 mm. In some embodiments, the RBS has a diameter from 10 to 15 m. In some embodiments, the RBS has a diameter from 5 to 7 mm (e.g., 5 mm, 6 mm, 7 mm). In some embodiments, the RBS has a diameter from 7 to 10 mm (e.g., 7 mm, 7.5 mm, 8 mm, 8.5 mm, 9 mm, 9.5 mm, 10 mm). In some embodiments, the RBS has a diameter from 9 to 12 mm (e.g., 9 mm, 9.5 mm, 10 mm, 10.5 mm, 11 mm, 11.5 mm, 12 mm). In some embodiments, the RBS has a diameter from 10 to 14 mm (e.g., 10 mm, 10.5 mm, 11 mm, 11.5 mm, 12 mm, 12.5 mm, 13 mm, 13.5 mm, 14 mm). In some embodiments, the RBS has a diameter from 12 to 16 mm (e.g., 12 mm, 12.5 mm, 13 mm, 13.5 mm, 14 mm, 14.5 mm, 15 mm, 15.5 mm, 16 mm). In some embodiments, the RBS has a diameter from 14 to 18 mm (e.g., 14 mm, 14.5 mm, 15 mm, 15.5 mm, 16 mm, 16.5 mm, 17 mm, 17.5 mm, 18 mm). In some embodiments, the RBS has a diameter of 3 mm. In some embodiments, the RBS has a diameter of 4 mm. In some embodiments, the RBS has a diameter of 5 mm. In some embodiments, the RBS has a diameter of 5 mm. In some embodiments, the RBS has a diameter of 6 mm. In some embodiments, the RBS has a diameter of 7 mm. In some embodiments, the RBS has a diameter of 8 mm. In some embodiments, the RBS has a diameter of 9 mm. In some embodiments, the RBS has a diameter of 10 mm. In some embodiments, the RBS has a diameter of 11 mm. In some embodiments, the RBS has a diameter of 12 mm. In some embodiments, the RBS has a diameter of 13 mm. In some embodiments, the RBS has a diameter of 14 mm. In some embodiments, the RBS has a diameter of 15 mm. In some embodiments, the RBS has a diameter of 16 mm. In some embodiments, the RBS has a diameter of 17 mm. In some embodiments, the RBS has a diameter of 18 mm. In some embodiments, the RBS has a diameter of 19 mm. In some embodiments, the RBS has a diameter of 20 mm. In some embodiments, the RBS has a diameter more than 20 mm.

In some embodiments, the RBS delivers a radiation dose of 1000 cGy (10 Gy) to the target. In some embodiments, the RBS delivers a radiation dose of 900 cGy to the target. In some embodiments, the RBS delivers a radiation dose of 800 cGy to the target. In some embodiments, the RBS delivers a radiation dose of 750 cGy to the target. In some embodiments, the RBS delivers a radiation dose of 600 cGy to the target. In some embodiments, the RBS delivers a radiation dose of 500 cGy to the target. In some embodiments, the RBS delivers a radiation dose of 400 cGy to the target. In some embodiments, the RBS delivers a radiation dose of 300 cGy to the target. In some embodiments, the RBS delivers a radiation dose of 200 cGy to the target. In some embodiments, the RBS delivers a radiation dose of 100 cGy to the target. In some embodiments, the RBS delivers a radiation dose of 50 cGy to the target. In some embodiments, the RBS delivers a radiation dose of 1100 cGy to the target. In some embodiments, the RBS delivers a radiation dose of 1200 cGy to the target. In some embodiments, the RBS delivers a radiation dose of 1300 cGy to the target. In some embodiments, the RBS delivers a radiation dose of 1500 cGy to the target. In some embodiments, the RBS delivers a radiation dose from 600 cGy and 1500 cGy to the target. In some embodiments, the RBS delivers a radiation dose from 50 cGy to 100 cGy. In some embodiments, the RBS delivers a radiation dose from 100 cGy to 150 cGy. In some embodiments, the RBS delivers a radiation dose from 150 cGy to 200 cGy. In some embodiments, the RBS delivers a radiation dose from 200 cGy to 250 cGy. In some embodiments, the RBS delivers a radiation dose from 250 cGy to 300 cGy. In some embodiments, the RBS delivers a radiation dose from 300 cGy to 350 cGy. In some embodiments, the RBS delivers a radiation dose from 350 cGy to 400 cGy. In some embodiments, the RBS delivers a radiation dose from 400 cGy to 450 cGy. In some embodiments, the RBS delivers a radiation dose from 450 cGy to 500 cGy. In some embodiments, the RBS delivers a radiation dose from 500 cGy to 550 cGy. In some embodiments, the RBS delivers a radiation dose from 550 cGy to 600 cGy. In some embodiments, the RBS delivers a radiation dose from 600 cGy to 650 cGy. In some embodiments, the RBS delivers a radiation dose from 650 cGy to 700 cGy. In some embodiments, the RBS delivers a radiation dose from 700 cGy to 750 cGy. In some embodiments, the RBS delivers a radiation dose from 750 cGy to 800 cGy. In some embodiments, the RBS delivers a radiation dose from 800 cGy to 850 cGy. In some embodiments, the RBS delivers a radiation dose from 850 cGy to 900 cGy. In some embodiments, the RBS delivers a radiation dose from 900 cGy to 950 cGy. In some embodiments, the RBS delivers a radiation dose from 950 cGy to 1000 cGy. In some embodiments, the RBS delivers a radiation dose from 1000 cGy to 1050 cGy. In some embodiments, the RBS delivers a radiation dose from 1050 cGy to 1100 cGy. In some embodiments, the RBS delivers a radiation dose from 1100 cGy to 1150 cGy. In some embodiments, the RBS delivers a radiation dose from 1150 cGy to 1200 cGy. In some embodiments, the RBS delivers a radiation dose from 1200 cGy to 1250 cGy. In some embodiments, the RBS delivers a radiation dose from 1250 cGy to 1300 cGy. In some embodiments, the RBS delivers a radiation dose from 1300 cGy to 1350 cGy. In some embodiments, the RBS delivers a radiation dose from 1350 cGy to 1400 cGy. In some embodiments, the RBS delivers a radiation dose from 1400 cGy to 1450 cGy. In some embodiments, the RBS delivers a radiation dose from 1450 cGy to 1500 cGy. In some embodiments, the RBS delivers a radiation dose from 1500 cGy to 1550 cGy. In some embodiments, the RBS delivers a radiation dose from 1550 cGy to 1600 cGy. In some embodiments, the RBS delivers a radiation dose from 1600 cGy to 1800 cGy. In some embodiments, the RBS delivers a radiation dose from 1800 cGy to 2000 cGy. In some embodiments, the RBS delivers a radiation dose of 600, 650, 700, 750, 800, 850, 900, 950, 1000, 1050, 1100, 1150, 1200, 1250, 1300, 1350, 1400, 1450, or 1500 cGy to the target. In some embodiments, the RBS delivers a radiation dose of 1500 to 3200 cGy. In some embodiments, the RBS delivers a radiation dose of 3200 to 8000 cGy. In some embodiments, the RBS delivers a radiation dose of 8000 cGy to 10000 cGy. In some embodiments, the RBS delivers a radiation dose of greater than 10000 cGy.

In some embodiments, the RBS delivers the prescribed dose in a time from 10 seconds to 20 minutes. In some embodiments, the RBS delivers the prescribed dose in a time from 20 seconds and 10 minutes. In some embodiments, the RBS delivers the prescribed dose in a time from 20 seconds to 60 seconds. In some embodiments, the RBS delivers the prescribed dose in a time from 30 seconds to 90 seconds. In some embodiments, the RBS delivers the prescribed dose in a time from 60 seconds to 90 seconds. In some embodiments, the RBS delivers the prescribed dose in a time from 90 seconds to 2 minutes. In some embodiments, the RBS delivers the prescribed dose in a time from 2 minutes to 3 minutes.

In some embodiments, the RBS delivers the prescribed dose in a time from 3 minutes to 4 minutes. In some embodiments, the RBS delivers the prescribed dose in a time from 3 minutes to 5 minutes. In some embodiments, the RBS delivers the prescribed dose in a time from 3 minutes to 6 minutes. In some embodiments, the RBS delivers the prescribed dose in a time from 4 minutes to 5 minutes. In some embodiments, the RBS delivers the prescribed dose in a time from 4 minutes to 6 minutes. In some embodiments, the RBS delivers the prescribed dose in a time from 5 minutes to 6 minutes. In some embodiments, the RBS delivers the prescribed dose in a time from 6 minutes to 7 minutes. In some embodiments, the RBS delivers the prescribed dose in a time from 7 minutes to 8 minutes. In some embodiments, the RBS delivers the prescribed dose in a time from 8 minutes to 9 minutes. In some embodiments, the RBS delivers the prescribed dose in a time from 9 minutes to 10 minutes. In some embodiments, the RBS delivers the prescribed dose in a time from 10 minutes to 12 minutes. In some embodiments, the RBS delivers the prescribed dose in a time from 12 minutes to 15 minutes. In some embodiments, the RBS delivers the prescribed dose in a time from 15 minutes to 20 minutes.

In some embodiments, the RBS delivers the prescribed dose in 25 seconds. In some embodiments, the RBS delivers the prescribed dose in 45 seconds. In some embodiments, the RBS delivers the prescribed dose in 60 seconds. In some embodiments, the RBS delivers the prescribed dose in 90 seconds. In some embodiments, the RBS delivers the prescribed dose in 2 minutes. In some embodiments, the RBS delivers the prescribed dose in 3 minutes. In some embodiments, the RBS delivers the prescribed dose in 4 minutes. In some embodiments, the RBS delivers the prescribed dose in 5 minutes. In some embodiments, the RBS delivers the prescribed dose in 6 minutes. In some embodiments, the RBS delivers the prescribed dose in 7 minutes. In some embodiments, the RBS delivers the prescribed dose in 8 minutes. In some embodiments, the RBS delivers the prescribed dose in 9 minutes. In some embodiments, the RBS delivers the prescribed dose in 10 minutes. In some embodiments, the RBS delivers the prescribed dose in 11 minutes. In some embodiments, the RBS delivers the prescribed dose in 12 minutes. In some embodiments, the RBS delivers the prescribed dose in 13 minutes. In some embodiments, the RBS delivers the prescribed dose in 14 minutes. In some embodiments, the RBS delivers the prescribed dose in 15 minutes. In some embodiments, the RBS delivers the prescribed dose in 16 minutes. In some embodiments, the RBS delivers the prescribed dose in 17 minutes. In some embodiments, the RBS delivers the prescribed dose in 18 minutes. In some embodiments, the RBS delivers the prescribed dose in 19 minutes. In some embodiments, the RBS delivers the prescribed dose in 20 minutes. In some embodiments, the RBS delivers the prescribed dose in a time frame greater than 20 minutes.

In some embodiments, a dose (e.g., a prescribed dose) may be delivered in a single application. In other embodiments, a dose (e.g., a prescribed dose) may be fractionated and applied in multiple applications. For example, in some embodiments, radiation (e.g., a prescribed dose) may be applied over the course of 2 applications. In some embodiments, radiation (e.g., a prescribed dose) may be applied over the course of 3 applications. In some embodiments, radiation (e.g., a prescribed dose) may be applied over the course of 4 applications. In some embodiments, radiation (e.g., a prescribed dose) may be applied over the course of 5 applications. In some embodiments, radiation (e.g., a prescribed dose) may be applied over the course of more than 5 applications. In some embodiments, radiation (e.g., a prescribed dose) may be applied over the course of 20 applications. In some embodiments, radiation (e.g., a prescribed dose) may be applied over the course of more than 20 applications.

Each application may deliver an equal sub-dose. In some embodiments, one or more of the sub-doses are different. For example, one or more of the sub-doses may be different so as to increase or decrease with each additional application.

According to one embodiment, a dose of radiation may be applied prior to the treatment procedure, e.g., surgery for implantation of a device, e.g., MIGS device, or other appropriate glaucoma procedure. For example, in some embodiments, a dose of radiation may be applied one or more days prior to a surgery (e.g., insertion of a device). In some embodiments, a dose of radiation may be applied within a 24-hour prior before a surgery (e.g., insertion of a device). In some embodiments, a dose of radiation may be applied just prior to a surgery (e.g., insertion of a device), e.g., 1 hour before, 30 minutes before, 15 minutes before, 5 minutes before 1 minute before, etc. In some embodiments, a dose of radiation may be applied during a procedure, e.g., for implantation of a device. In some embodiments, a dose of radiation may be applied right after a device (e.g., MIGS device) is implanted or a hole is created, e.g., within 1 minute, 2 minutes, 3 minutes, 5 minutes, 10 minutes, etc.). In some embodiments, a dose of radiation may be applied before an incision is made into the conjunctiva. In some embodiments, a dose of radiation may be applied after an incision is made into the conjunctiva. In other embodiments, a dose of radiation may be applied after a surgery (e.g., insertion of a device). In some embodiments, a dose of radiation may be applied within a 24-hour period after a surgery (e.g., insertion of a device). In some embodiments, a dose of radiation may be applied within one to two days after a surgery (e.g., insertion of a device). In some embodiments, a dose of radiation may be applied within 2 or more days after a surgery (e.g., insertion of a device). In some embodiments the dose may be applied any time after the glaucoma surgery. In some embodiments, the dose is applied months or years after the glaucoma surgery. For example, a dose may be given to patients that did not receive a dose during surgery but at a future date have scar or needling procedures to break up scar tissue.

(B) Brachytherapy Applicator

The present invention also provides brachytherapy applicators for applying the beta radiation to the target in the eye. In certain embodiments, the applicator may feature the RBS fixedly attached to the applicator. For example, the applicator may be manufactured such that the RBS is integrated into the applicator prior to distribution or surgical use. In some embodiments, the applicator is manufactured to accept the RBS at a later time. For example, the applicator may be manufactured and distributed, and the RBS may be attached to or inserted into the applicator prior to its use in surgery.

The applicator may be constructed from any appropriate material, such as a biocompatible material or a combination of materials. Non-limiting examples of biocompatible materials include, but are not limited to, metals (for example, stainless steel, titanium, gold), ceramics and polymers.

In some embodiments, one or more components of the invention (e.g., applicator) are constructed from a material that can further shield the user from the RBS. In some embodiments, a material having a low atomic number (Z) may be used for shielding (e.g., polymethyl methacrylate). In some embodiments, one or more layers of material are used for shielding, wherein an inner layer comprises a material having a low atomic number (e.g., polymethyl methacrylate) and an outer layer comprises lead.

As an example, in some embodiments, the present invention is a device loaded from a Ruthenium-106 cow with an activity of rhodium-106 providing for the prescribed dose. The device can be applied to the target volume to deliver the full activity of its contents. For example, the device may be placed over the target lesion for 10 half-lives (300 seconds), delivering all its radioactive energy and consuming the rhodium-106, depleting it to palladium.

As an example, in some embodiments, the present invention is an applicator constructed containing Strontinum-90/Yttrium-90 radioisotopes in secular equilibrium. In some embodiments, the Sr-90/Y-90 is in a sealed source brachytherapy device, e.g., constructed of stainless steel. The source may be constructed to project a dose of about 1,000 cGy per unit time into a sufficient portion of the adjacent Planning Treatment Volume, e.g., to contain the conjunctival tissue to a depth of 0.3 mm. The source may be attached to or integrated into a brachytherapy applicator, and a radiation attenuation mask may be attached to the source or integrated with the source. In some embodiments, the source or attenuation mask or other component may be covered with a sterile barrier. The present invention is not limited to this embodiment, and variations and combinations of the disclosed features are also covered in the scope of this application.

Methods

As previously discussed, the present invention provides methods for applying beta radiation to a target of the eye, for example the hole and/or site of a bleb formed by a MIMS device or procedure. Without wishing to limit the present invention to any theory or mechanism, it is believed that the use of beta radiation to treat the MIMS-associated hole and/or site of the bleb is advantageous because the application of beta radiation can be rapid and simple, and the effects can be long lasting. Further, beta radiation may be advantageous since it does not require post-operative compliance.

Other methods include methods of inhibiting or reducing fibrogenesis in a hole and/or bleb associated with a MIMS procedure; methods of inhibiting or reducing inflammation in a hole and/or bleb or associated with a MIMS procedure.

Other methods include methods to maintain the function of a hole and/or bleb associated with MIMS, methods to enhance the function of a MIMS procedure, e.g., by maintaining a functional hole and/or bleb, methods to enhance the success of MIMS, methods for repairing a failed trabeculectomy, methods for repairing a failed MIMS, methods to reduce intraocular pressure (IOP), methods to maintain a healthy IOP, methods for treating glaucoma, etc.

The methods herein may comprise applying beta radiation (to a target) before a MIMS procedure, during a MIMS procedure, or after a MIMS procedure (or a combination thereof). For example, a MIMS procedure may be performed using a MIMS device within the eye.

The methods further comprise applying beta radiation to the target, e.g., the site of the bleb, the MIMS-associated hole, etc. In some embodiments, the target is from 2 to 5 mm in diameter. In some embodiments, the target is from 5 to 12 mm in diameter. In some embodiments, the target is from 0.3 mm to 0.5 mm in thickness.

In some embodiments, the methods herein may further comprise introducing a drug to a site (e.g., a site of the MIMS procedure, a site of the bleb, a site of the hole, a different part of the eye, etc.) in addition to beta radiation. For example, in some embodiments, the methods herein comprise applying an antimetabolite (e.g., mitomycin-c or 5-fluorouracil) in addition to beta radiation. In some embodiments, the methods comprise administering pharmaceutical eye drops or a liquid anti-metabolite or other liquid drug. Application of one or more drugs may be before, during, and/or after a surgical procedure, e.g., a MIMS procedure.

The methods, systems, and devices herein may also be used to treat previously formed blebs and/or holes, e.g., those formed by MIMS, MIGS, trabeculetomy, etc. (Without wishing to limit the present invention to any theory or mechanism, it is believed that treating scar tissue formation on a bleb formed by a trabeculectomy procedure is different than treating a newly-created (and scar tissue-free) bleb at the time of the trabeculectomy.)

In some embodiments, methods herein comprise applying beta radiation to a bleb and/or hole (formed by MIMS, MIGS, trabeculetcomy, etc.) that is failing or has failed. In some embodiments, the methods herein comprise applying beta radiation to a hole and/or bleb (formed by MIMS, MIGS, trabeculetcomy, etc.) that has formed scar tissue. In some embodiments, the methods herein comprise applying beta radiation to a hole and/or bleb (formed by MIMS, MIGS, trabeculetcomy, etc.) in a patient whose intraocular pressure (IOP) has increased.

The methods, systems, and devices herein may be used for needling procedures, e.g., procedures to blebs and/or holes to free or remove scar tissue and/or cystic structures about the bleb and/or hole and/or surgery site that may later arise from wound healing or scarring or inflammatory responses. Needling procedures may affect surgical site morphology, restore the function of the surgery and/or lower the IOP.

In some embodiments, the methods herein may feature applying beta radiation to a bleb or hole (e.g., a bleb from a glaucoma device or procedure such as a MIMS procedure, trabeculectomy, etc.) that is about to undergo needling, e.g., from 3 to 6 weeks before, from 1 to 3 weeks before, from 3 to 7 days before, from 24 to 72 hours before, from 12 to 24 hours before, from 6 to 12 hours before, from 3 to 6 hours before, from 2 to 3 hours before, from 1 to 2 hours before, from 30 to 60 minutes before, from 20 to 30 minutes before, from 10 to 20 minutes before, from 1 to 10 minutes before, etc. In some embodiments, methods herein may feature applying the beta radiation to a bleb (e.g., a bleb from a glaucoma device or procedure such as a MIMS procedure, trabeculectomy, etc.) that has previously undergone needling, e.g., from 0.5 to 10 minutes after, from 10 to 20 minutes after, from 20 to 30 minutes after, from 30 to 60 minutes after, from 1 to 2 hours after, from 2 to 3 hours after, from 3 to 6 hours after, from 6 to 12 hours after, from 12 to 24 hours after, from 24 to 72 hours after, from 3 to 7 days after, from 1-3 weeks after, from 3 to 6 weeks after, etc.

Radioactive Needle

The present invention also features a radioactive needle for use in combination with MIMS, wherein the radioactive needle delivers beta radiation to at least a portion of the drainage channel formed in a MIMS procedure.

EXAMPLE 1

Mims Device Operative Procedure

Preparation, Assembly, and Quality Assurance

The sterile packaging that contains the MIMS hand-held disposable probe device which includes a cutting tool is checked by examining for damage or breach of the sterile barrier. Finding none, the package is opened, and the sterile MIMS tool device assembly placed on a sterile field. The hand-held disposable probe is connected to the transmission cable assembly that leads back to the motor and controller. The device assembly is checked by depressing the foot petal switch, and the rotating action of the cutting tool is observed to be working properly (FIG. 2). A cover that guards the cutting tool before being used is removed prior to handing the device to the surgeon.

Surgical Application

First, the surgical field is readied according to routine surgical preparation for glaucoma filtering surgery and the patient is anesthetized. Surgeons may opt to use a regional block to minimize the potential for patient or ocular movements that may lead to iatrogenic trauma. Below describes an Ab Externo procedure and an Ab Interno procedure for MIMS.

Ab Externo Procedure for MIMS:

A lid speculum is placed. The eye is rotated to a downward gaze position. This may be assisted by the use of a probe placed against the sclera providing traction (for example the distal end of a Vera Hook placed against the eye). The conjunctiva is grasped with 0.12 forceps 5 mm to 7 mm from the limbus. The MIMS surgical tool is introduced via a small conjunctival opening 10 mm to 15 mm from the corneoscleral limbus and advanced gently towards the limbus. The MIMS device tip is positioned at the penetration site. The penetration site is at the sclera-corneal junction. Other entry points are also possible. For example, the target penetration site is 3 mm posterior to the anterior limbus. The device is pushed through the sclera into the anterior chamber entering at Descemet's membrane, anterior to the iris and on the plane of the iris.

Correct positioning of the tool is assessed using a surgical microscope. The tip is visualized in the anterior chamber through the transparent cornea. Once the tip is inserted into the anterior chamber and proper positioning is ascertained, the MIMS foot pedal is pressed to activate the device blade action according to a predefined action of rotations per minute (RPM) and duration. For example, a blade of 300 μm (micrometers) outer diameter (OD), with programed action of 8,000 RPM for 0.5 seconds. This creates the drainage channel. Other combinations of blade OD, duration, RMP, and number of cutting iterations or pulses are possible. The MIMS device is then withdrawn from the eye. Following this sclerostomy, the surgeon examines the eye under the microscope to confirm formation of the intraoperative bleb as the aqueous humor drains from the anterior chamber through the sclerostomy to form a bleb under the conjunctivae.

As described herein, at the conclusion of MIMS surgery, the conjunctival area may be exposed to beta irradiation with a radioactive brachytherapy source (RBS)-containing delivery device. In some embodiments, the target area may be exposed to beta radiation at the conclusion of the MIMS procedure, prior to MIMS surgery, a time point following MIMS surgery, a combination thereof, etc.

Rb Interno Procedure for MIMS:

A small bleb is formed by injection under the conjunctiva (e.g., Balanced Saline Solution or air) followed by ophthalmic viscoelastic, or the like. The subconjunctival needle injection may be assisted by lifting the conjunctiva with 0.12 forceps 5 mm to 7 mm from the limbus. The globe is stabilized with a probe placed against the sclera. A 1.8 mm Keratome blade is used to enter the anterior chamber. The incision is made 180° from the intended MIMS location. The incision is angled toward the targeted quadrant of the stent placement. The anterior chamber is stabilized with the addition of ophthalmic viscoelastic.

The MIMS surgical tool tip is inserted through the corneal incision and the probe is advanced through the anterior chamber. Visualization by gonioscopy may be used in guiding the injector to the target location in the angle. The surgical instrument tip is placed just anterior to the trabecular meshwork in the angle. Once the tip is properly located in the angle, the MIMS cutting device blade action is activated. In some embodiments the switch is a foot pedal. The cutting tool blade is advanced through the sclera into the subconjunctival space at the bleb site. The cutting tool is retracted and with that the tissue is also extracted. This creates a small iatrogenic fistula or channel through the sclera. The MIMS device is then withdrawn from the eye.

Following this sclerostomy, the surgeon examines the eye under the microscope to confirm aqueous humor drains from the anterior chamber through the sclerostomy into the bleb under the conjunctivae. Viscoelastic is evacuated and thoroughly rinsed from the anterior chamber. If present, any blood is thoroughly removed from the anterior chamber. Following this step, constant irrigation of balanced salt solution into the anterior chamber maybe preformed to prime the implant. The surgeon also thoroughly hydrates all incisions to ensure that pressure and a formed anterior chamber are maintained. The clear cornea incision may be closed with fluid hydration. For a leaking incision, a 10-0 nylon suture may also be placed.

As described herein, the conjunctival area may be exposed to beta irradiation with a radioactive brachytherapy source (RBS)-containing delivery device. In some embodiments, the target area may be exposed to beta radiation at the conclusion of the MIMS procedure, prior to MIMS surgery, a time point following MIMS surgery, a combination thereof, etc.

EXAMPLE 2

Beta Radiation Application Surgical Procedure

Preparation and Assembly

Figure 4:
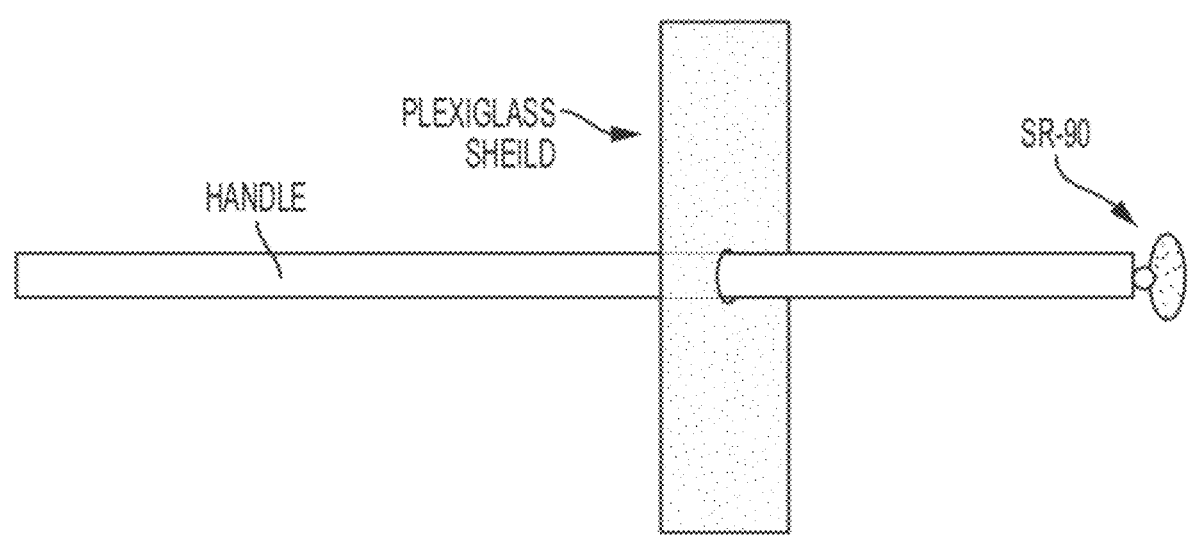
FIG. 4 shows an illustration of a Sr-90 ophthalmic beta applicator with a plexiglass shield.
Figure 5:
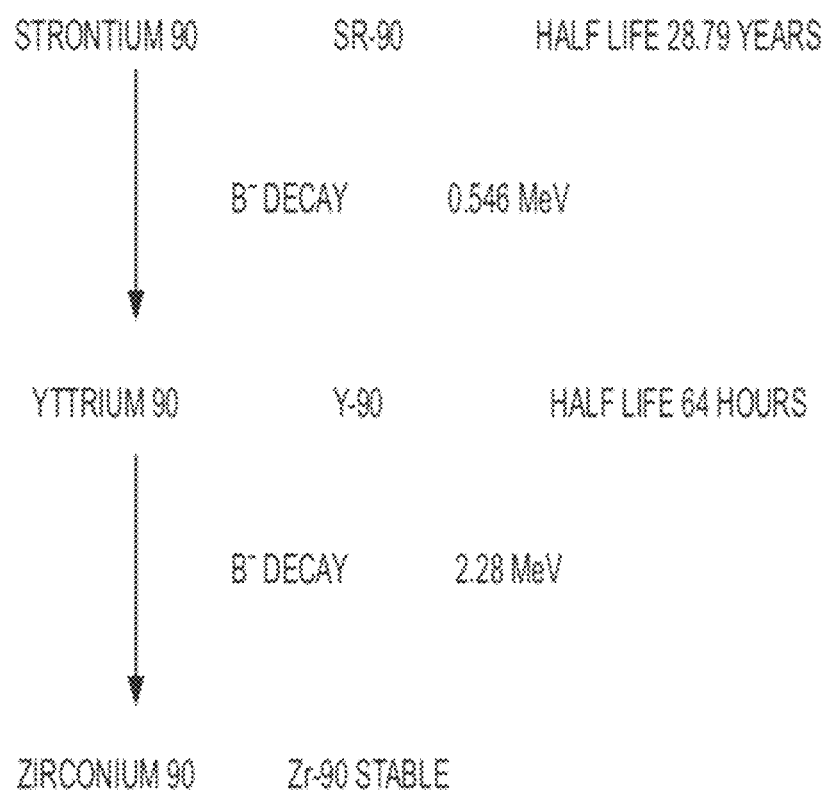
FIG. 5 shows a schematic illustration of the radioactive decay of Strontium 90 and the resulting beta emission.
Figure 6A:
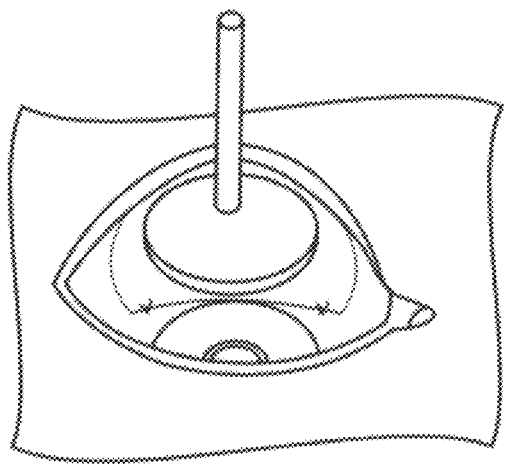
FIG. 6A shows a drawing illustrating the positioning on the eye of a beta radiation applicator.
Figure 6B:
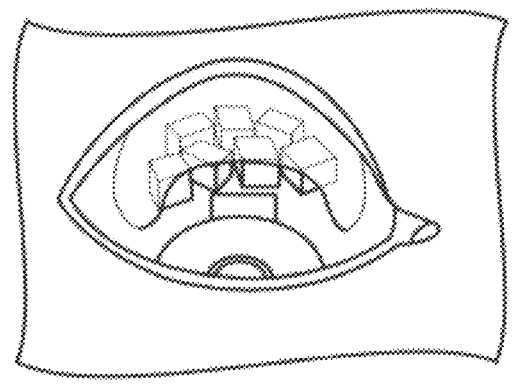
FIG. 6B shows a drawing illustrating the positioning on the eye of sponges soaked with MMC.
Figure 7:
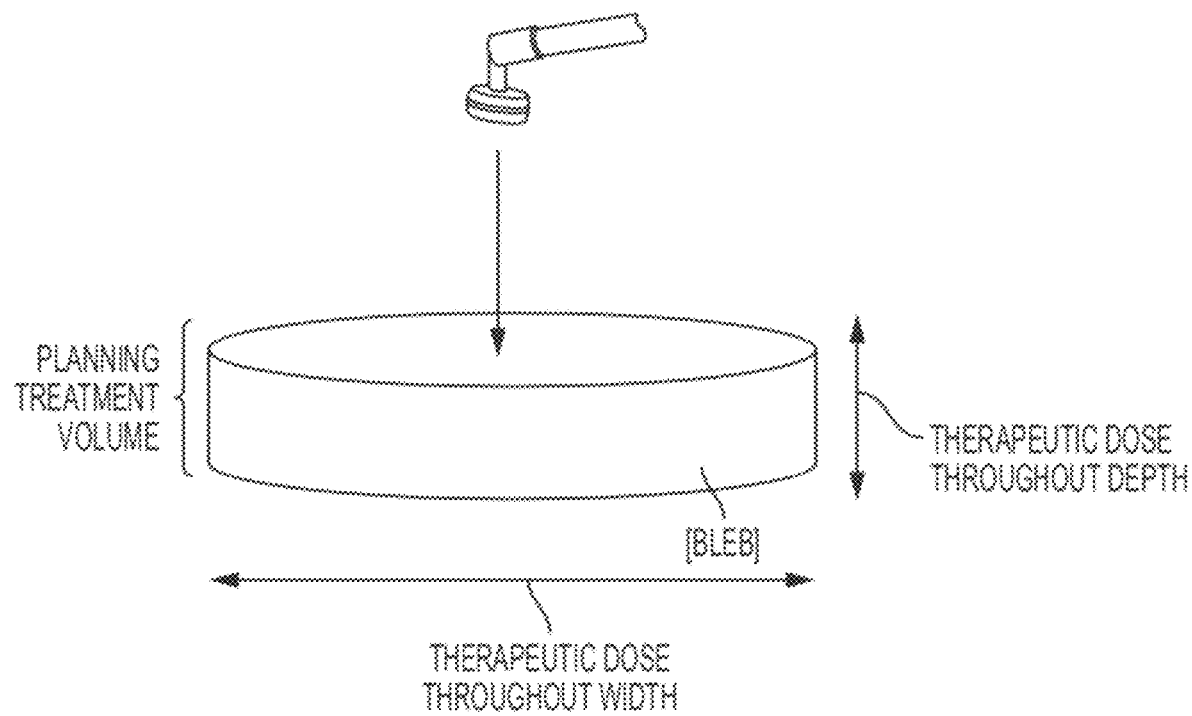
FIG. 7 shows a schematic view of the planning treatment volume of the bleb, wherein a therapeutic dose is applied throughout the width and depth of the target.
Figure 8:
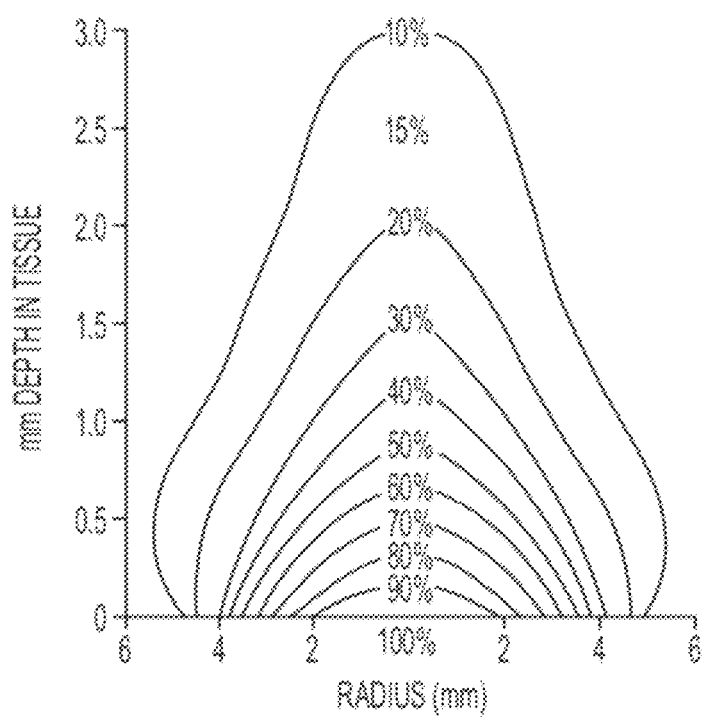
FIG. 8 shows a series of isodose curves of a Sr-90 beta applicator and the penetration depth of the radiation in tissue.

The Beta Ophthalmic Applicator device assembly procedure is performed behind a plexiglass beta shield (for example, the Large Dual Angle Beta Radiation Shield, Universal Medical Inc.; FIG. 4). The medical technician or medical physicist opens the Radioisotope Brachytherapy Source (RBS) storage container. The RBS is removed from its container using remote handling techniques (for example, long forceps). The RBS is placed on a clean field.

The Manual Brachytherapy Applicator (MBA) assembly is a single-use sterile-packed device. Its packaging is checked by examining for damage or breach of the sterile barrier. Finding none, the applicator package is opened, and the applicator assembly placed on a sterile field.

The applicator assembly consists of a handle and RBS cap. Using aseptic technique and remote handling techniques, the RBS is loaded into the applicator. The handle is attached, and the sterile cap is attached. Care is taken not to cross contaminate the exterior of the sterile applicator with the clean RBS.

The radiation output is confirmed consistent with standards of quality assurance in radiation therapy (for example see: Palmer, Antony L., Andrew Nisbet, and David Bradley. "Verification of high dose rate brachytherapy dose distributions with EBT3 Gafchromic film quality control techniques." Physics in medicine and biology 58.3 (2013): 497). In one method of quality assurance, the applicator is applied to radiographic film in sterile overwrap for a specified dwell time (for example Gafchromic® film, Ashland Inc.). The overwrap is removed. The medical physicist checks the area of application for evidence of film exposure.

The device is placed into a sterile plexiglass beta transport box (for example the IBI Beta-Gard Acrylic Storage Container—Large, Universal Medical Inc.) and the box placed on the operative Mayo stand.

Previously the decayed activity of the RBS has been calculated to determine the contemporary dose per unit time (for example, cGy/second). The decay calculation methodology is known to those skilled in medical physics and is also described in the NRC Information Notice 96-66: United States Nuclear Regulatory Commission, Office of Nuclear Material Safety and Safeguards, Washington D.C. 20555, Dec. 13, 1996. The dwell time for the total prescribed dose is then calculated. As an example, the prescription dose is 1,000 cGy to a center point of 0.19 mm depth from the conjunctival surface. As an example, the decayed activity of the RBS is 30 cGy/second at a water equivalent depth of 0.19 mm. In this example, the dwell time is calculated to be about 33 seconds, providing a 990 cGy dose.

Surgical Application

The beta therapy is applied following completion of the glaucoma surgery. The eyelid remains retracted with an eyelid speculum. The eye is rotated to a downward gaze position by the use of a probe placed against the sclera providing traction (for example the distal end of a Vera Hook placed against the eye). This allows better visual and surgical access to the superior conjunctiva.

The ophthalmic surgeon removes the Manual Brachytherapy Applicator device from its shielded box. The distal end (active end) of the applicator is placed on the conjunctivae in a position just superior to the limbus. The diameter of the applicator is envelops the bleb or a portion of the bleb to the diameter of the applicator. The area of application also envelops the majority of the distal end of the MIMS sclerotomy, also enveloping the conjunctiva that directly overlays the sclerotomy orifice.

Figure 9:
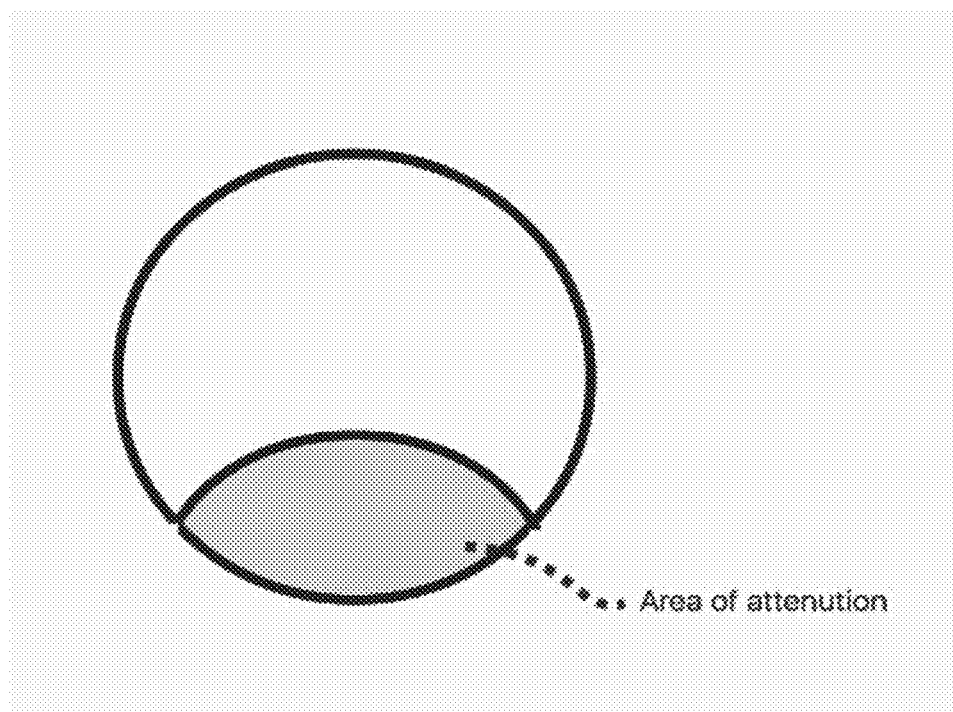
FIG. 9 shows that a sterile cap has the functionality of a Castroviejo Mask that attenuates the radiation to the cornea.
Figure 10:
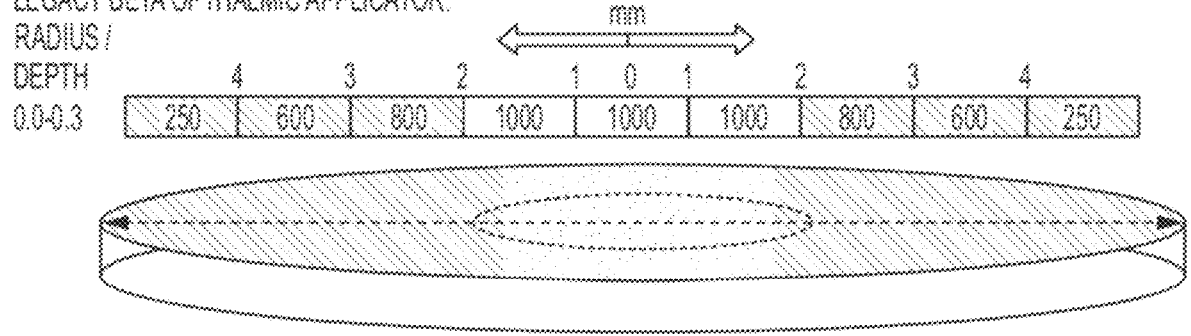
FIG. 10 shows a schematic view of an example of previous radiation applicators that only treat the center part of the target, thereby under-dosing the peripheral area and/or overdosing the center.
Figure 11:
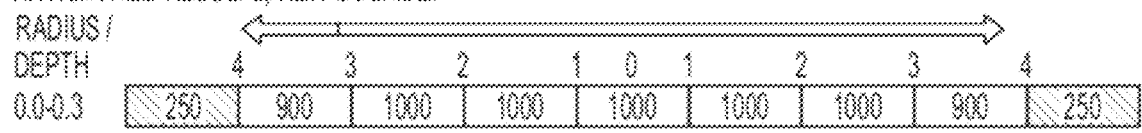
FIG. 11 shows a schematic view of an example of the optimized dose delivery used in the present invention, wherein the dose applied across the target is more uniform as compared to that shown in FIG. 12. Iterative computer simulations of output dosimetry may inform an optimized design of device.
Figure 11:
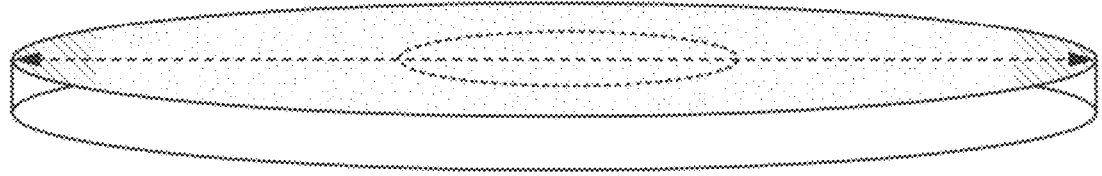
Figure 12:
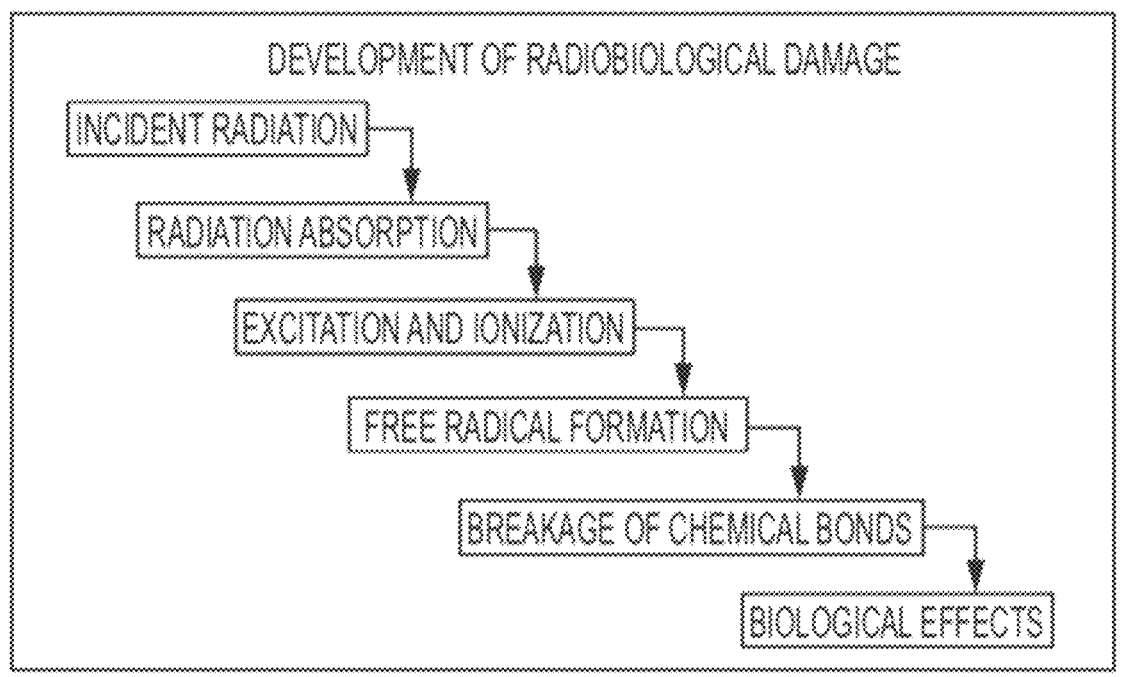
FIG. 12 shows a schematic illustrating the development of radiobiological damage.
Figure 13:
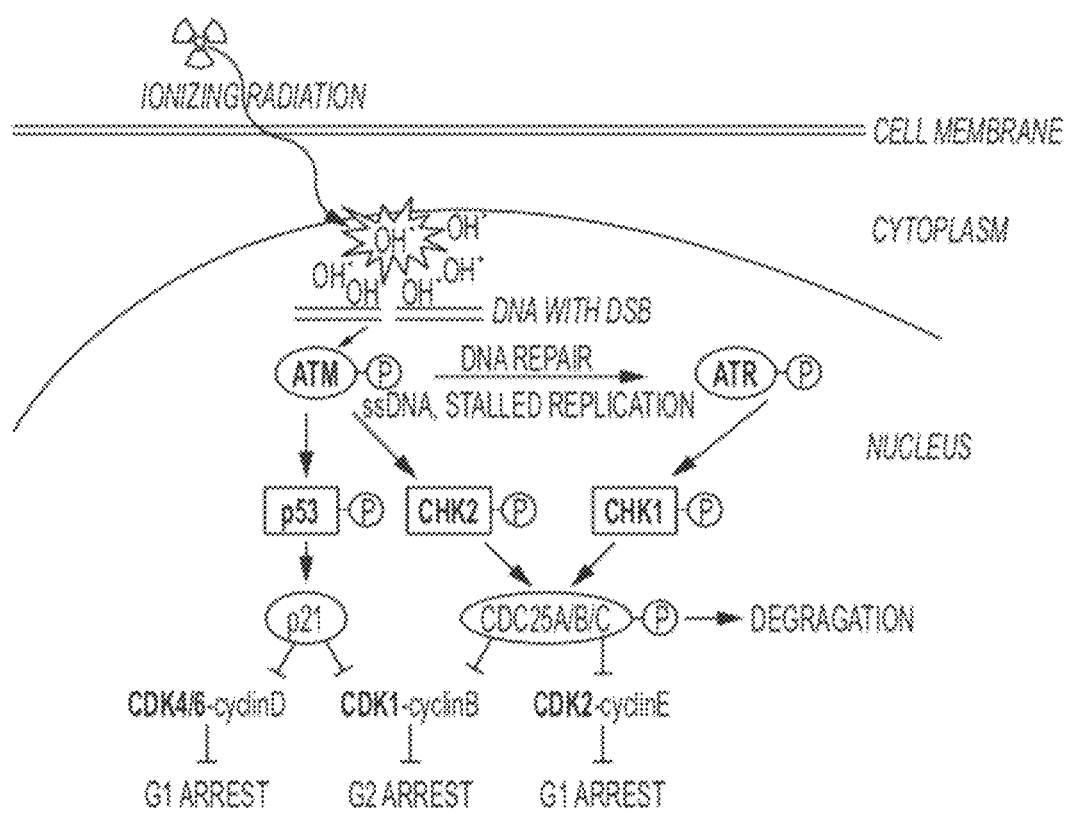
FIG. 13 shows a schematic of the induction of cell cycle arrest after irradiation. The hydroxyl radical is the most important aqueous radical induced by ionizing radiation (symbolized by the sinuous arrow and the trefoil) affecting the integrity of DNA (parallel lines) by induction of double strand breaks (DSB, gap in DNA). Subsequently, the ATM (ataxia-telangiectasia mutated) kinase is activated by phosphorylation (encircled P) and, in turn, phosphorylates p53. ATR (ataxia-telangiectasia and RAD3-related) is activated by single-stranded DNA and stalled replication forks arising from the repair process. Activated p53 acts as a transcription factor and causes the expression of the cyclin-dependent kinase (CDK) inhibitor p21, which induces cell cycle arrest during the G1 and G2 phases. On the other hand, activation of CHK1 and CHK2 (checkpoint kinase-1 and -2) leads to phosphorylation of the three CDC25 (cell division cycle 25) isoforms, resulting in its degradation. As a consequence, CDC25 no longer activates CDK2 or CDK1 (cyclin-dependent kinase), and thus, the cell cycle is stopped in the G1 or G2 phase, respectively. Arrows symbolize activation; bar-headed lines symbolize inhibition. See Maier, 2016, Int. J. Mol. Sci. 17, 102; doi:10.3390/ijms17010102
Figure 14:
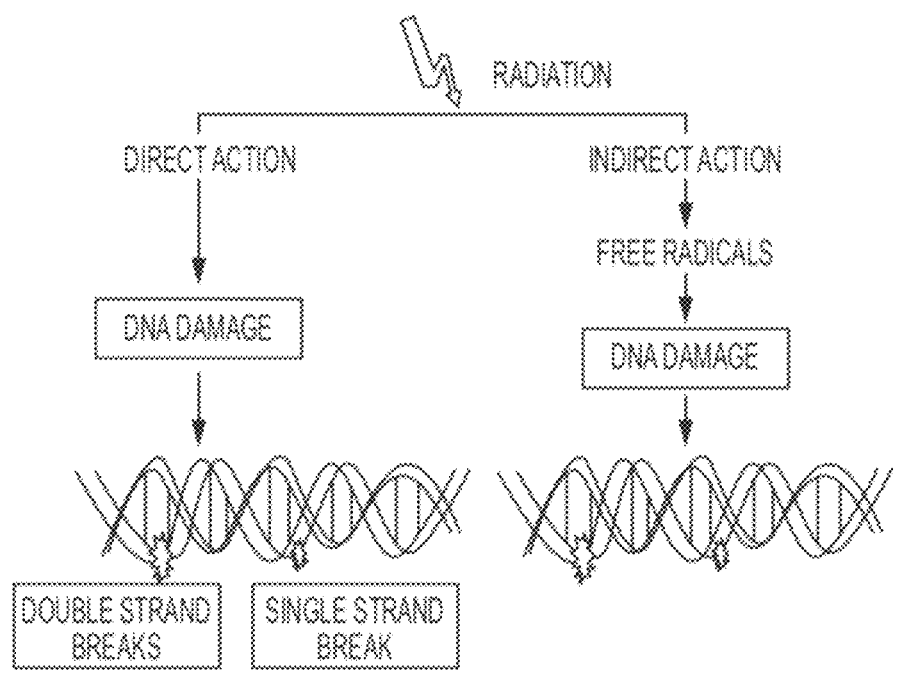
FIG. 14 shows a schematic view of how radiation can act in two ways: (1) It induces ionizations directly on the cellular molecules and causes damage; and (2) it can act indirectly by producing free radicals that are derived from the ionization or excitation of water in the cells.
Figure 15:
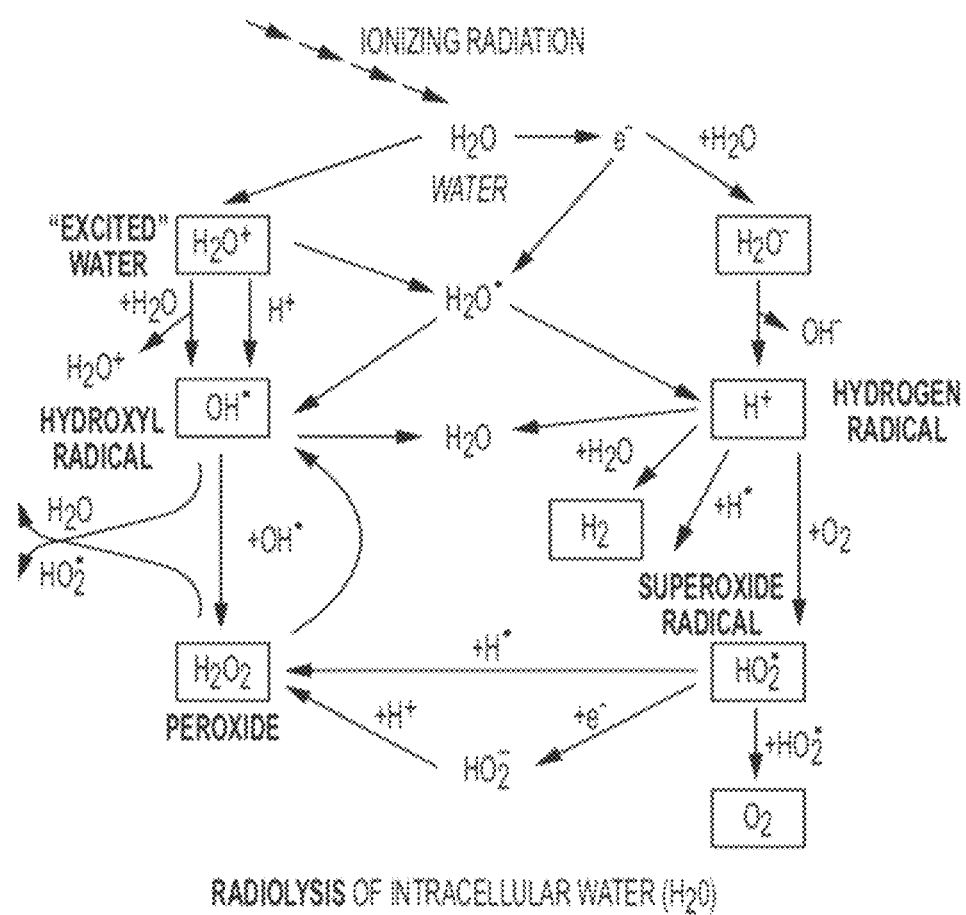
FIG. 15 shows a schematic of the radiolysis of intracellular water.

Other alignments of the placement of the beta applicator are also possible. For example, the applicator is placed over the sclera and conjunctivae so as to also include the limbus and a portion of the cornea. In some embodiments, the sterile cap has the functionality of a Castroviejo Mask that attenuates the radiation to the cornea (FIG. 9).

The Manual Brachytherapy Applicator is held in place for the specified dwell time. In some embodiments, the dwell time has been programmed into a count-down clock. Following the specified dwell time, the Manual Ophthalmic Brachytherapy Applicator is removed from the operative field and returned to the shielded acrylic box.

Following the MIMS surgery and at the conclusion of the application of beta radiation, the speculum is removed and topical antibiotic and steroid are administered to the eye and the eye patched.

Following the surgery, the Manual Brachytherapy Applicator is disassembled behind the acrylic beta shield. The Radioisotope Brachytherapy Source is returned to its storage container. The disposable portions of the device are discarded in a manner consistent with appropriate disposal of biological waste (for example "red bag" waste). The MIMS hand-held disposable probe device which includes a cutting tool is disconnected from the transmission cable assembly. The cutting tool is removed and placed in the sharps disposal container. The handle is discarded in a manner consistent with appropriate disposal of biological waste (for example "red bag" waste).

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of treating glaucoma or reducing intraocular pressure (IOP) in an eye of a patient, said method comprising:
    performing minimally invasive micro sclerostomy in the eye of the patient to form a drainage channel from an anterior chamber to allow aqueous humor to drain into a bleb in a subconjunctival space or space between a conjunctiva and Tenon's capsule; and
    b. applying a therapeutic dose of beta radiation from a radioisotope that emits beta radiation to a target area of the eye, wherein the target area is tissue surrounding a rim of the drainage channel; wherein the therapeutic dose of beta radiation at any point of the target area is within 10% of a dose of beta radiation at any other point on the target;
    wherein the method is effective for reducing an Intraocular Pressure (IOP) of the eye or treating glaucoma.

2. The method of claim 1 further comprising administering a drug to the target area before, after, or both before and after applying the therapeutic amount of beta radiation to the target area.

3. The method of claim 1, wherein the beta radiation is applied to the target area before performing minimally invasive micro sclerostomy, after performing minimally invasive micro sclerostomy, or both before and after performing minimally invasive micro sclerostomy.

4. The method of claim 1, wherein the radioisotope that emits beta radiation comprises Strontium-90 (Sr-90), Phosphorus-32 (P-32), Ruthenium 106 (Ru-106), Yttrium 90 (Y-90), or a combination thereof.

5. The method of claim 1, wherein the target area further comprises at least a portion of the bleb above the drainage channel.

6. The method of claim 1, wherein the target further comprises at least a portion of the bleb above the drainage channel and at least a portion of a perimeter of the bleb.

7. The method of claim 1, wherein the target further comprises at least a portion of the bleb above the drainage channel, at least a portion of a perimeter of the bleb, and at least a portion of the bleb between the perimeter and the portion above the drainage channel.

8. The method of claim 1, wherein the therapeutic dose is from 500-1000 cGy.

9. The method of claim 1, wherein the therapeutic dose is from 450-1050 cGy.

10. A method of maintaining a functioning drainage bleb or drainage channel in an eye of a patient being treated with minimally invasive micro sclerostomy, the eye having a drainage channel from an anterior chamber to allow aqueous humor to drain into a bleb in a subconjunctival space or space between a conjunctiva and Tenon's capsule, said method comprising:
    applying a therapeutic dose of beta radiation from a radioisotope that emits beta radiation to a target area of the eye, wherein the target area is tissue surrounding a rim of the drainage channel; wherein the therapeutic dose of beta radiation at any point of the target area is within 10% of a dose of beta radiation at any other point on the target;
    wherein the therapeutic dose of beta radiation is effective to maintain drainage of the bleb or drainage channel.

11. The method of claim 10 further comprising the step of performing MIMS in the eye of the patient to form the drainage channel from an anterior chamber to allow aqueous humor to drain into a bleb in a subconjunctival space or space between a conjunctiva and Tenon's capsule.

12. The method of claim 10 further comprising administering a drug to the target area before, after, or both before and after applying the therapeutic amount of beta radiation to the target area.

13. The method of claim 10, wherein the radioisotope that emits beta radiation comprises Strontium-90 (Sr-90), Phosphorus-32 (P-32), Ruthenium 106 (Ru-106), Yttrium 90 (Y-90), or a combination thereof.

14. The method of claim 10, wherein the target area further comprises at least a portion of the bleb above the drainage channel.

15. The method of claim 10, wherein the target further comprises at least a portion of the bleb above the drainage channel and at least a portion of a perimeter of the bleb.

16. The method of claim 10, wherein the target further comprises at least a portion of the bleb above the drainage channel, at least a portion of a perimeter of the bleb, and at least a portion of the bleb between the perimeter and the portion. above the drainage channel.

17. The method of claim 10, wherein the therapeutic dose is from 500-1000 cGy.

18. The method of claim 10, wherein the therapeutic dose is from 450-1050 cGy.

19. A method of inhibiting or reducing fibrogenesis and inflammation in a bleb of an eye or a drainage channel of an eye being treating with minimally invasive micro sclerostomy, the eye having a drainage channel from an anterior chamber to allow aqueous humor to drain into a bleb in a subconjunctival space or space between a conjunctiva and Tenon's capsule, said method comprising:

applying a therapeutic dose of beta radiation from a radioisotope that emits beta radiation to a target area of the eye, wherein the target area is tissue surrounding a rim of the drainage channel; wherein the therapeutic dose of beta radiation at any point of the target area is within 10% of a dose of beta radiation at any other point on the target;

wherein the therapeutic dose of beta radiation causes inhibition or reduction of a fibrotic process and inflammation that otherwise leads to bleb failure or drainage channel failure.

20. The method of claim 19 further comprising administering a drug to the target area before, after, or both before and after applying the therapeutic amount of beta radiation to the target area.

21. The method of claim 19, wherein the radioisotope that emits beta radiation comprises Strontium-90 (Sr-90), Phosphorus-32 (P-32), Ruthenium 106 (Ru-106), Yttrium 90 (Y-90), or a combination thereof.

22. The method of claim 19, wherein the target area further comprises at least a portion of the bleb above the drainage channel.

23. The method of claim 19, wherein the target further comprises at least a portion of the bleb above the drainage channel and at least a portion of a perimeter of the bleb.

24. The method of claim 19, wherein the target further comprises at least a portion of the bleb above the drainage channel, at least a portion of a perimeter of the bleb, and at least a portion of the bleb between the perimeter and the portion above the drainage channel.

25. The method of claim 19, wherein the therapeutic dose is from 500-1000 cGy.

26. The method of claim 19, wherein the therapeutic dose is from 450-1050 cGy.

* * * * *